US011819212B2

(12) United States Patent
Jones et al.

(10) Patent No.: US 11,819,212 B2
(45) Date of Patent: Nov. 21, 2023

(54) STAPLE FORMING FEATURES FOR CIRCULAR SURGICAL STAPLER

(71) Applicant: Cilag GmbH International, Zug (CH)

(72) Inventors: Shannon L. Jones, Cincinnati, OH (US); Jason L. Harris, Lebanon, OH (US); Frederick E. Shelton, IV, Hillsboro, OH (US); Gregory J. Bakos, Mason, OH (US)

(73) Assignee: Cilag GmbH International, Zug (CH)

( * ) Notice: Subject to any disclaimer, the term of this patent is extended or adjusted under 35 U.S.C. 154(b) by 100 days.

(21) Appl. No.: 17/489,965

(22) Filed: Sep. 30, 2021

(65) Prior Publication Data
US 2023/0049242 A1 Feb. 16, 2023

Related U.S. Application Data

(63) Continuation of application No. 17/401,428, filed on Aug. 13, 2021.

(51) Int. Cl.
*A61B 17/00* (2006.01)
*A61B 17/115* (2006.01)
(Continued)

(52) U.S. Cl.
CPC ....... *A61B 17/1155* (2013.01); *A61B 17/1114* (2013.01); *A61B 2017/07228* (2013.01);
(Continued)

(58) Field of Classification Search
CPC ............ A61B 2017/07264; A61B 2017/07228
See application file for complete search history.

(56) References Cited

U.S. PATENT DOCUMENTS

| 4,047,654 A | 9/1977 | Alvarado |
| 4,848,328 A | 7/1989 | Laboureau et al. |

(Continued)

FOREIGN PATENT DOCUMENTS

| EP | 1875870 A1 | 1/2008 |
| EP | 2157918 | 3/2010 |

(Continued)

OTHER PUBLICATIONS

International Search Report and Written Opinion dated Nov. 14, 2022 for Application No. PCT/IB2022/057444, 12 pgs.

(Continued)

*Primary Examiner* — Chelsea E Stinson
(74) *Attorney, Agent, or Firm* — Frost Brown Todd LLP

(57) ABSTRACT

A surgical instrument includes a stapling assembly and an anvil that releasably couple together to compress and staple tissue. The stapling assembly includes a body having a longitudinal axis, a deck member, and a knife member surrounding the longitudinal axis. The deck member includes a deck surface having an imaginary centerline that surrounds the longitudinal axis, a first deck surface portion extending along a first angular range of the deck surface about the longitudinal axis, and a second deck surface portion extending along a second angular range of the deck surface about the longitudinal axis. A first array of staple openings is disposed on the first deck surface portion and is arranged in a first orientation relative to the deck surface centerline. A second array of staple openings is disposed on the second deck surface portion and is arranged in a second orientation relative to the deck surface centerline.

20 Claims, 17 Drawing Sheets

(51) Int. Cl.
*A61B 17/11* (2006.01)
*A61B 17/072* (2006.01)

(52) U.S. Cl.
CPC ............... *A61B 2017/07264* (2013.01); *A61B 2017/07285* (2013.01); *A61B 2017/1132* (2013.01)

(56) References Cited

U.S. PATENT DOCUMENTS

| | | | |
|---|---|---|---|
| 5,292,053 | A | 3/1994 | Bilotti et al. |
| 5,309,927 | A * | 5/1994 | Welch ................. A61B 17/115 128/898 |
| 5,333,773 | A | 8/1994 | Main et al. |
| 5,350,104 | A | 9/1994 | Main et al. |
| 5,533,661 | A | 7/1996 | Main et al. |
| 5,993,468 | A * | 11/1999 | Rygaard ............... A61B 17/115 606/151 |
| 6,616,686 | B2 | 9/2003 | Coleman et al. |
| 7,056,330 | B2 | 6/2006 | Gayton |
| 7,422,138 | B2 * | 9/2008 | Bilotti ................. A61B 17/115 227/19 |
| 7,824,426 | B2 | 11/2010 | Racenet et al. |
| 8,143,870 | B2 | 3/2012 | Ng et al. |
| 8,328,063 | B2 | 12/2012 | Milliman et al. |
| 8,413,870 | B2 * | 4/2013 | Pastorelli ............ A61B 17/105 227/181.1 |
| 8,613,384 | B2 * | 12/2013 | Pastorelli ............ A61B 17/072 227/179.1 |
| 8,789,738 | B2 | 7/2014 | Knodel et al. |
| 8,910,847 | B2 | 12/2014 | Nalagatla et al. |
| 9,016,541 | B2 * | 4/2015 | Viola .................. A61B 17/072 227/176.1 |
| 9,192,387 | B1 | 11/2015 | Holsten et al. |
| 9,402,628 | B2 * | 8/2016 | Beardsley .......... A61B 17/0682 |
| 9,713,469 | B2 | 7/2017 | Leimbach et al. |
| 9,782,171 | B2 * | 10/2017 | Viola ................. A61B 17/1155 |
| 9,848,874 | B2 | 12/2017 | Kostrzewski |
| 9,907,552 | B2 | 3/2018 | Measamer et al. |
| 9,936,949 | B2 | 4/2018 | Measamer et al. |
| 10,285,705 | B2 | 5/2019 | Shelton, IV et al. |
| 10,639,040 | B2 | 5/2020 | Penna et al. |
| 10,709,452 | B2 | 7/2020 | DiNardo et al. |
| 10,856,867 | B2 | 12/2020 | Shelton, IV et al. |
| 10,925,607 | B2 | 2/2021 | Penna et al. |
| 11,147,559 | B2 | 10/2021 | Wise et al. |
| 11,241,232 | B2 | 2/2022 | Guerrera |
| 11,284,890 | B2 | 3/2022 | Nalagatla et al. |
| 11,291,450 | B2 | 4/2022 | Nalagatla et al. |
| 11,523,821 | B2 | 12/2022 | Harris et al. |
| 2003/0018236 | A1 * | 1/2003 | Adams ............... A61B 1/00071 600/128 |
| 2006/0291981 | A1 | 12/2006 | Viola et al. |
| 2007/0175963 | A1 * | 8/2007 | Bilotti ................. A61B 17/115 227/179.1 |
| 2011/0011916 | A1 * | 1/2011 | Levine ................ A61B 17/115 227/179.1 |
| 2011/0017800 | A1 * | 1/2011 | Viola .................. A61B 17/115 227/175.1 |
| 2012/0325893 | A1 * | 12/2012 | Pastorelli ............ A61B 17/115 227/177.1 |
| 2014/0027493 | A1 | 1/2014 | Jankowski |
| 2014/0158747 | A1 | 6/2014 | Measamer et al. |
| 2015/0083772 | A1 | 3/2015 | Miller et al. |
| 2016/0278768 | A1 * | 9/2016 | Johnson ............... A61B 17/068 |
| 2017/0119397 | A1 * | 5/2017 | Harris ................ A61B 17/1222 |
| 2018/0132849 | A1 | 5/2018 | Miller et al. |
| 2018/0235635 | A1 | 8/2018 | Rekstad et al. |
| 2018/0242974 | A1 | 8/2018 | Guerrera et al. |
| 2018/0325508 | A1 | 11/2018 | Aronhalt et al. |
| 2020/0038017 | A1 | 2/2020 | Hess et al. |
| 2020/0054339 | A1 | 2/2020 | Scirica et al. |
| 2020/0229814 | A1 | 7/2020 | Amariglio et al. |

FOREIGN PATENT DOCUMENTS

| | | |
|---|---|---|
| EP | 2649949 A1 | 10/2013 |
| EP | 3225176 A1 | 10/2017 |
| EP | 3225179 A1 | 10/2017 |
| EP | 3245958 A1 | 11/2017 |
| EP | 3130292 B1 | 8/2018 |
| EP | 3173030 B1 | 10/2019 |
| EP | 3643252 A1 | 4/2020 |
| WO | WO 2001/054594 A1 | 8/2001 |
| WO | WO 2002/009595 A1 | 2/2002 |
| WO | WO 2005/115254 A2 | 12/2005 |
| WO | WO 2008/141288 A1 | 11/2008 |
| WO | WO 2020/249487 A1 | 12/2020 |

OTHER PUBLICATIONS

International Search Report and Written Opinion dated Jan. 27, 2023 for Application No. PCT/IB2022/057446, 19 pgs.
International Search Report and Written Opinion dated Nov. 23, 2022 for Application No. PCT/IB2022/057449, 15 pgs.
International Search Report and Written Opinion dated Jan. 25, 2023 for Application No. PCT/IB2022/057442, 20 pgs.
International Search Report and Written Opinion dated Nov. 14, 2022 for Application No. PCT/IB2022/057443, 12 pgs.
International Search Report and Written Opinion dated Nov. 24, 2022 for Application No. PCT/IB2022/057451, 13 pgs.
U.S. Appl. No. 17/401,391, entitled, "Methods of Forming an Anastomosis Between Organs with an Expandable Pattern," filed Aug. 13, 2021.
U.S. Appl. No. 17/401,428, entitled, "Staple Forming Features for Circular Surgical Stapler," filed Aug. 13, 2021.
U.S. Appl. No. 17/401,430, entitled, "Non-Circular End Effector Features for Surgical Stapler," filed Aug. 13, 2021.
U.S. Appl. No. 17/401,439, entitled, "Circular Surgical Stapler End Effector Having Staple Line Alignment Feature," filed Aug. 13, 2021.
U.S. Appl. No. 17/401,444, entitled, "Circular Surgical Stapler for Forming Pattern of Non-Tangential Staples," filed Aug. 13, 2021.
U.S. Appl. No. 17/401,451, entitled, "Circular Surgical Stapler Having Staples with Expandable Crowns," filed Aug. 13, 2021.
U.S. Appl. No. 17/401,460, entitled, "Circular Surgical Stapler for Forming Cross-Pattern of Staples," filed Aug. 13, 2021.

* cited by examiner

STAPLE FORMING FEATURES FOR CIRCULAR SURGICAL STAPLER

BACKGROUND

This application is a continuation of U.S. application Ser. No. 17/401,428, entitled "Staple Forming Features for Circular Surgical Stapler," filed Aug. 13, 2021, published as U.S. Pub. No. 2023/0047471 on Feb. 16, 2023.

A circular surgical stapler may be used to form an anastomosis between two organ portions of a patient's digestive tract. Examples of circular surgical staplers are described in U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pat. No. 9,936,949, entitled "Surgical Stapling Instrument with Drive Assembly Having Toggle Features," issued Apr. 10, 2018; U.S. Pat. No. 9,907,552, entitled "Control Features for Motorized Surgical Stapling Instrument," issued Mar. 6, 2018; U.S. Pat. No. 9,713,469, entitled "Surgical Stapler with Rotary Cam Drive," issued Jul. 25, 2017; U.S. Pub. No. 2018/0132849, entitled "Staple Forming Pocket Configurations for Circular Surgical Stapler Anvil," published May 17, 2018, now abandoned; and U.S. Pat. No. 10,709,452, entitled "Methods and Systems for Performing Circular Stapling," issued Jul. 14, 2020. The disclosure of each of the above-cited U.S. Patent Publications and U.S. Patents is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
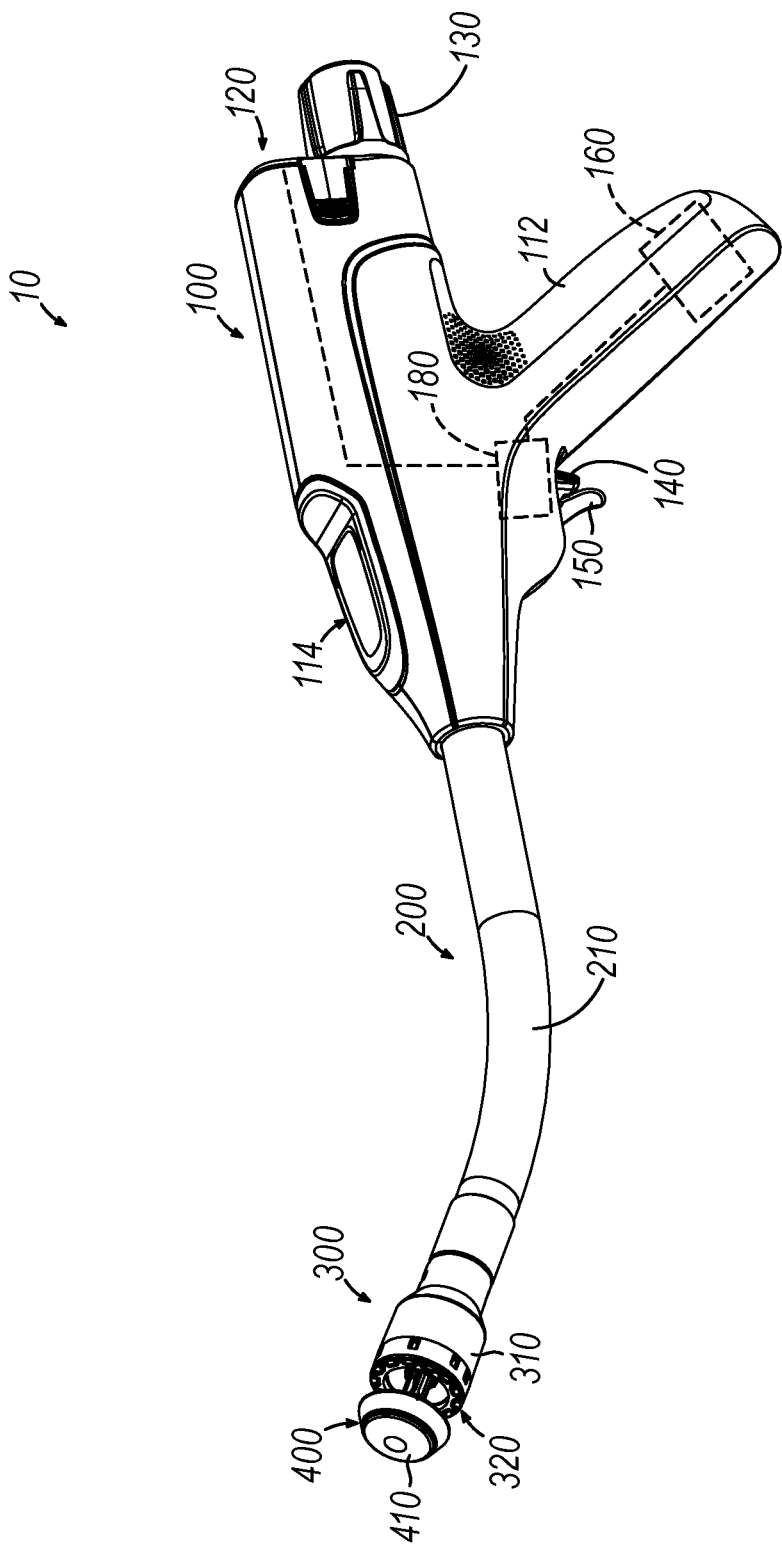
FIG. 1 depicts a perspective view of an exemplary circular surgical stapler that includes a handle assembly, a shaft assembly, and an end effector having a stapling head assembly and an anvil.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose described herein.

I. OVERVIEW OF EXEMPLARY CIRCULAR SURGICAL STAPLING INSTRUMENT

Figure 2:
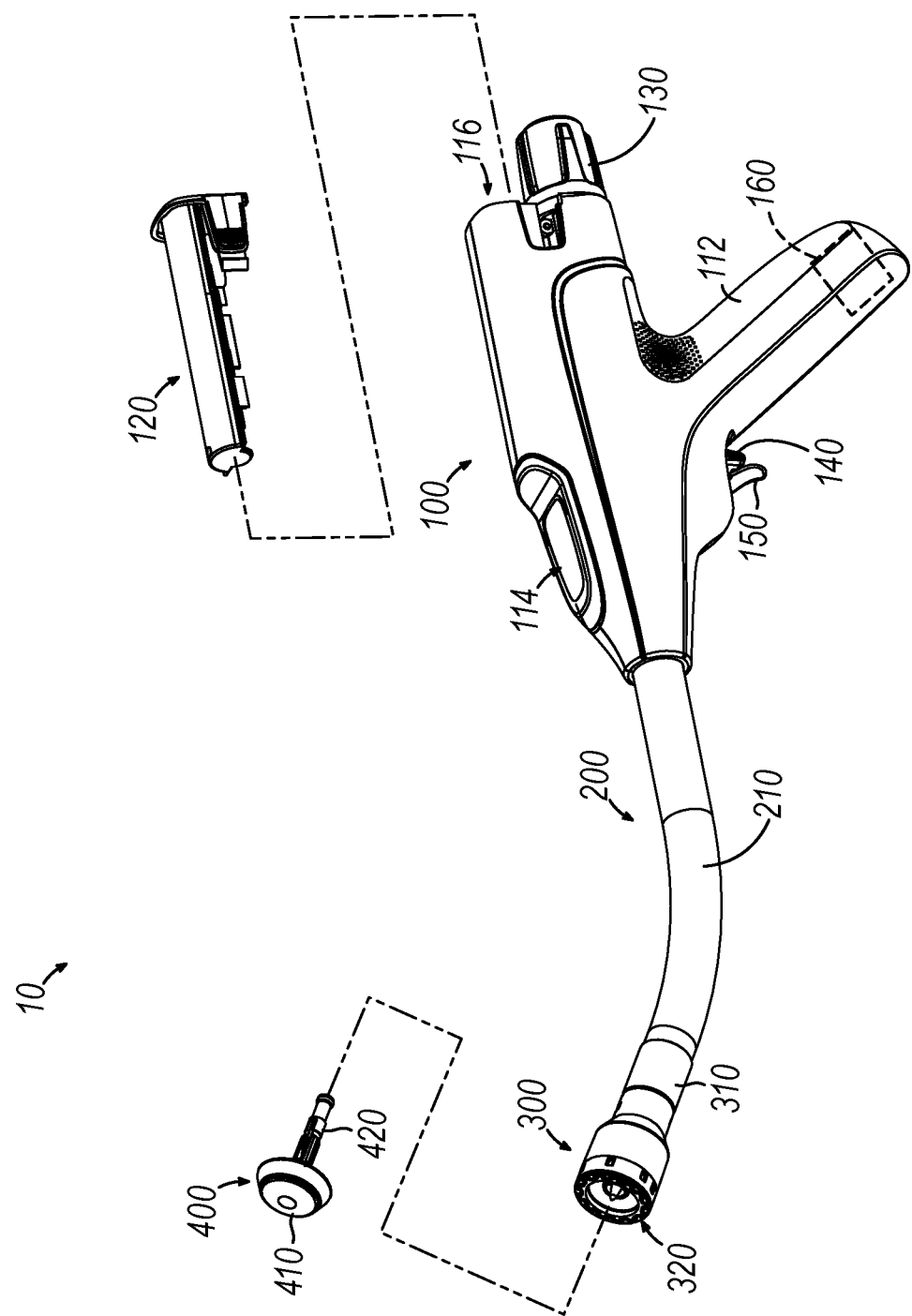
FIG. 2 depicts a perspective view of the circular stapler of FIG. 1, with a battery pack removed from the handle assembly and the anvil separated from the stapling head assembly.

FIGS. 1-2 depict an exemplary circular surgical stapling instrument (10) that may be used to provide an end-to-end, side-to-side, or end-to-side anastomosis between two sections of an anatomical lumen such as a portion of a patient's digestive tract. Instrument (10) of this example includes a body assembly in the form of a handle assembly (100), a shaft assembly (200) extending distally from handle assembly (100), a stapling head assembly (300) at a distal end of shaft assembly (200), and an anvil (400) configured to releasably couple and cooperate with stapling head assembly (300) to clamp, staple, and cut tissue. Instrument (10) further includes a removable battery pack (120) operable to provide electrical power to a motor (160) housed within handle assembly (100), as will be described in greater detail below.

As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A rotatable knob (130) at the proximal end of handle assembly (100) is rotatable to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the clamped tissue.

A. Exemplary Anvil

Figure 3:
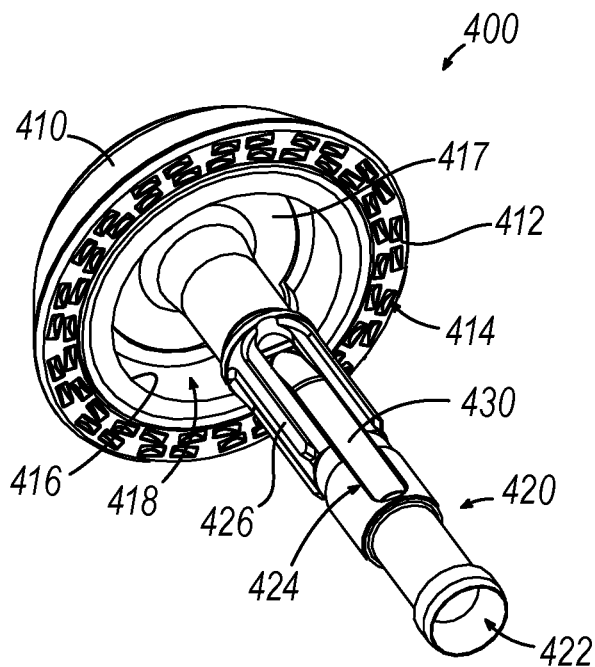
FIG. 3 depicts a perspective view of the anvil of the circular stapler of FIG. 1.

As best seen in FIG. 3, anvil (400) of the present example comprises a head (410) and a shank (420). Head (410) includes a proximal stapling surface (412) that defines a plurality of staple forming pockets (414). Staple forming pockets (414) are arranged in two concentric annular arrays in the present example. Staple forming pockets (414) are configured to deform staples as the staples are driven into staple forming pockets (414). Proximal stapling surface (412) terminates at an inner edge (416), which defines an outer boundary of an annular recess (418) surrounding shank (420). A breakable washer (417) is positioned within annular recess (418) and is configured to provide the operator with a tactile and audible indication that a distal firing stroke has been completed, in addition to serving as a cutting board, as described in greater detail below.

Shank (420) defines a bore (422) and includes a pair of pivoting latch members (430). Latch members (430) are positioned within bore (422) such that distal ends (434) are positioned at the proximal ends of lateral openings (424), which are formed through the sidewall of shank (420). Latch members (430) thus act as retaining clips. This allows anvil (400) to be removably secured to an actuatable closure member in the form of a trocar (330) of stapling head assembly (300), as will be described in greater detail below. Shank (420) of anvil (400) and trocar (330) of stapling head assembly (300) thus cooperate with one another as coupling members.

B. Exemplary Stapling Head Assembly

Figure 4:
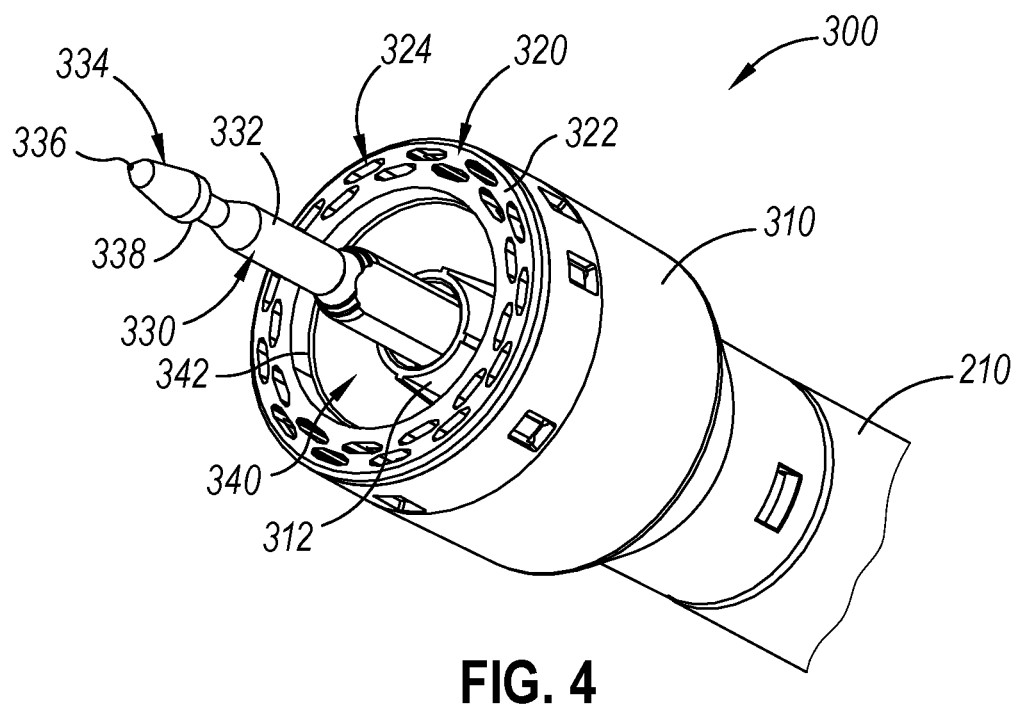
FIG. 4 depicts a perspective view of the stapling head assembly of the circular stapler of FIG. 1.
Figure 5:
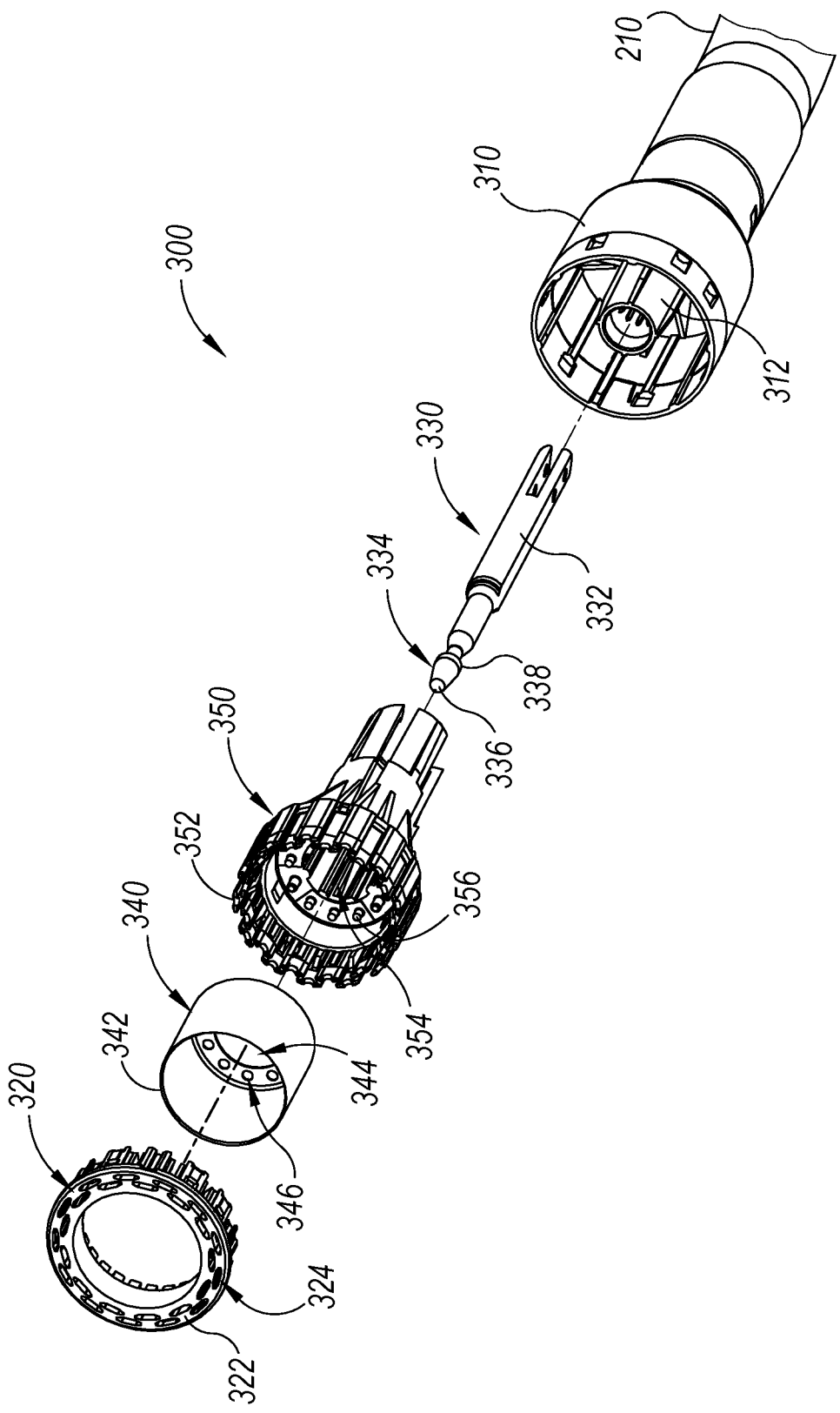
FIG. 5 depicts an exploded perspective view of the stapling head assembly of FIG. 4.

As best seen in FIGS. 4 and 5, stapling head assembly (300) of the present example is coupled to a distal end of shaft assembly (200) and comprises a tubular body member (310) and a staple driver member (350) slidably housed therein. Body member (310) includes a distally extending cylindraceous inner core member (312) positioned coaxially therein. Body member (310) is fixedly secured to an outer sheath (210) of shaft assembly (200), and body member (310) and outer sheath (210) thus serve together as a mechanical ground for stapling head assembly (300).

Trocar (330) is positioned coaxially within inner core member (312) of body member (310). As will be described in greater detail below, trocar (330) is operable to translate distally and proximally relative to body member (310) in response to rotation of knob (130) relative to casing (110) of handle assembly (100). Trocar (330) comprises a shaft (332) and a head (334). Head (334) includes a pointed tip (336) and a radially inwardly extending proximal surface (338). Head (334) and the distal portion of shaft (332) are configured for insertion into bore (422) of anvil (400). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit provided by latch members (430).

Staple driver member (350) is operable to actuate longitudinally within body member (310) in response to activation of motor (160) as will be described in greater detail below. As shown best in FIG. 5, staple driver member (350) of the present example includes two distally presented concentric annular arrays of staple drivers (352). Staple drivers (352) are arranged to correspond with the arrangement of staple forming pockets (414) of anvil (400). Thus, each staple driver (352) is configured to drive a corresponding staple distally into a corresponding staple forming pocket (414) when stapling head assembly (300) is actuated (or "fired"). Staple driver member (350) also defines a bore (354) that is configured to coaxially and slidably receive core member (312) of body member (310). An annular array of studs (356) project distally from a distally presented surface surrounding bore (354).

A cylindraceous knife member (340) is coaxially positioned within a distally-opening central recess of staple driver member (350) that communicates with bore (354). Knife member (340) includes a distally presented, sharp circular cutting edge (342). Knife member (340) is sized such that knife member (340) defines an outer diameter that is just smaller than the diameter defined by the radially inner-most surfaces of the inner annular array of staple drivers (352). Knife member (340) also defines a central opening that is configured to coaxially receive core member (312) of body member (310). An annular array of openings (346) formed in knife member (340) is configured to mate with the annular array of studs (356) of staple driver member (350), such that knife member (340) is fixedly secured to staple driver member (350) via studs (356) and openings (346).

An annular deck member (320) is fixedly secured to a distal end of body member (310). Deck member (320) includes a distally presented stapling surface in the form of a deck surface (322) having two concentric annular arrays of staple openings (324). Staple openings (324) are arranged to align with the arrangement of staple drivers (352) of staple driver member (350) and staple forming pockets (414) of anvil (400) described above. Each staple opening (324) is configured to slidably receive and provide a pathway for a corresponding staple driver (352) to drive a corresponding staple distally through deck member (320) and into a corresponding staple forming pocket (414) when stapling head assembly (300) is actuated. As best seen in FIG. 4, deck member (320) has a central opening that defines an inner diameter that is just slightly larger than the outer diameter defined by knife member (340). Deck member (320) is thus configured to permit knife member (340) to translate longitudinally through the central opening concurrently with longitudinal translation of staple driver member (350). In particular, knife member (340) is configured to actuate relative to deck member (340) between a proximal retracted position and a distal extended position, where cutting edge (342) is proximal to deck surface (322) in the proximal retracted position and distal to deck surface (322) in the distal extended position.

C. Exemplary Shaft Assembly

Figure 6:
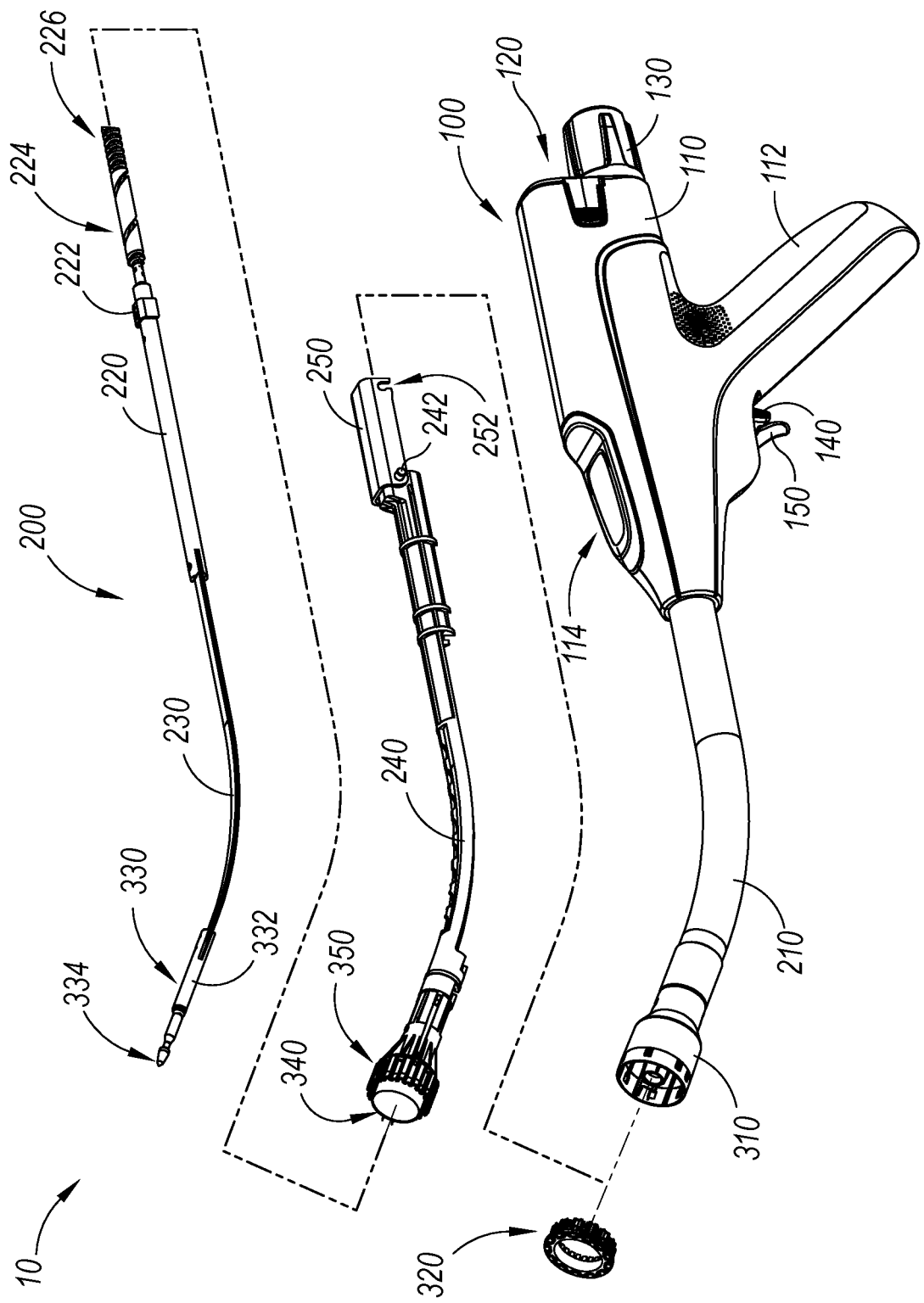
FIG. 6 depicts an exploded perspective view of the circular stapler of FIG. 1, with portions of the shaft assembly shown separated from each other.

FIG. 6 shows various components of shaft assembly (200), which operatively couple components of stapling head assembly (300) with components of handle assembly (100). In particular, and as noted above, shaft assembly (200) includes an outer sheath (210) that extends between handle assembly (100) and body member (310) and includes a medial portion that extends along a curved path.

Shaft assembly (200) further includes a trocar actuation rod (220) having a proximal end operatively coupled with rotatable knob (130) and a distal end coupled with a flexible trocar actuation band assembly (230), the assembly of which is slidably housed within outer sheath (210). The distal end of trocar actuation band assembly (230) is fixedly secured to the proximal end of trocar shaft (332), such that trocar (330) will translate longitudinally relative to outer sheath (210) in response to translation of trocar actuation band assembly (230) and trocar actuation rod (220) relative to outer sheath (210), which occurs in response to rotation of rotatable knob (130). A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a section of coarse helical threading (224) and a section of fine helical threading (226) proximal to coarse helical threading (224), which are configured to control a rate of longitudinal advancement of trocar actuation rod (220), as described in greater detail below.

Shaft assembly (200) further includes a stapling head assembly driver (240) that is slidably housed within outer sheath (210) and about the combination of trocar actuation rod (220) and trocar actuation band assembly (230). Stapling head assembly driver (240) includes a distal end that is fixedly secured to the proximal end of staple driver member (350), a proximal end secured to a drive bracket (250) via a pin (242), and a flexible section disposed therebetween. It should therefore be understood that staple driver member (350) will translate longitudinally relative to outer sheath (210) in response to translation of stapling head assembly driver (240) and drive bracket (250) relative to outer sheath (210).

D. Exemplary Handle Assembly and User Input Features

As shown in FIG. 1, handle assembly (100) includes a casing (110) having a lower portion that defines an obliquely oriented pistol grip (112) and an upper portion that supports a user interface feature (114) and releasably receives a battery pack (120), as described in greater detail below. Handle assembly (100) further includes several features that are operable to actuate anvil (400) and stapling head assembly (300). In particular, handle assembly (100) includes a rotatable knob (130), a safety trigger (140), a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, and then translate proximally at a relatively fast rate, in response to rotation of knob (130).

It should be understood that when anvil (400) is coupled with trocar (330), rotation of knob (130) will provide corresponding translation of anvil (400) relative to stapling head assembly (300). It should also be understood that knob (130) may be rotated in a first angular direction (e.g., clockwise) to retract anvil (400) proximally toward stapling head assembly (300); and in a second angular direction (e.g., counterclockwise) to extend anvil (400) distally away from stapling head assembly (300). Knob (130) may thus be used to adjust a gap distance (d) between opposing stapling surfaces (412, 322) of anvil (400) and stapling head assembly (300) until a suitable gap distance (d) has been achieved, for example as shown in FIG. 7C described below.

Firing trigger (150) is operable to activate motor (160) to thereby actuate stapling head assembly (300) to staple and cut tissue clamped between anvil (400) and stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). For instance, safety trigger (140) may be blocked from rotating from an engaged position to a disengaged position until the position of anvil (400) relative to stapling head assembly (300) is within a predefined range. Accordingly, until the anvil position is within the predefined range, actuation of firing trigger (150) is blocked by safety trigger (140), thereby inhibiting firing of stapling head assembly (300).

Firing trigger (150) is operable to actuate a switch of motor activation module (180) (FIG. 1) when firing trigger (150) is pivoted proximally to a fired position. Motor activation module (180) is in communication with battery pack (120) and motor (160), such that motor activation module (180) is configured to provide activation of motor (160) with electrical power from battery pack (120) in response to firing trigger (150) actuating the switch of motor activation module (180). Thus, motor (160) will be activated when firing trigger (150) is pivoted. This activation of motor (160) will actuate stapling head assembly (300) via drive bracket (250), as described in greater detail below.

E. Exemplary Anastomosis Procedure with Circular Stapling Instrument

FIGS. 7A-7E show instrument (10) being used to form an anastomosis (70) between two tubular anatomical structures (20, 40). By way of example only, the tubular anatomical structures (20, 40) may comprise sections of a patient's esophagus, colon, or other portions of the patient's digestive tract, or any other tubular anatomical structures.

Figure 7A:
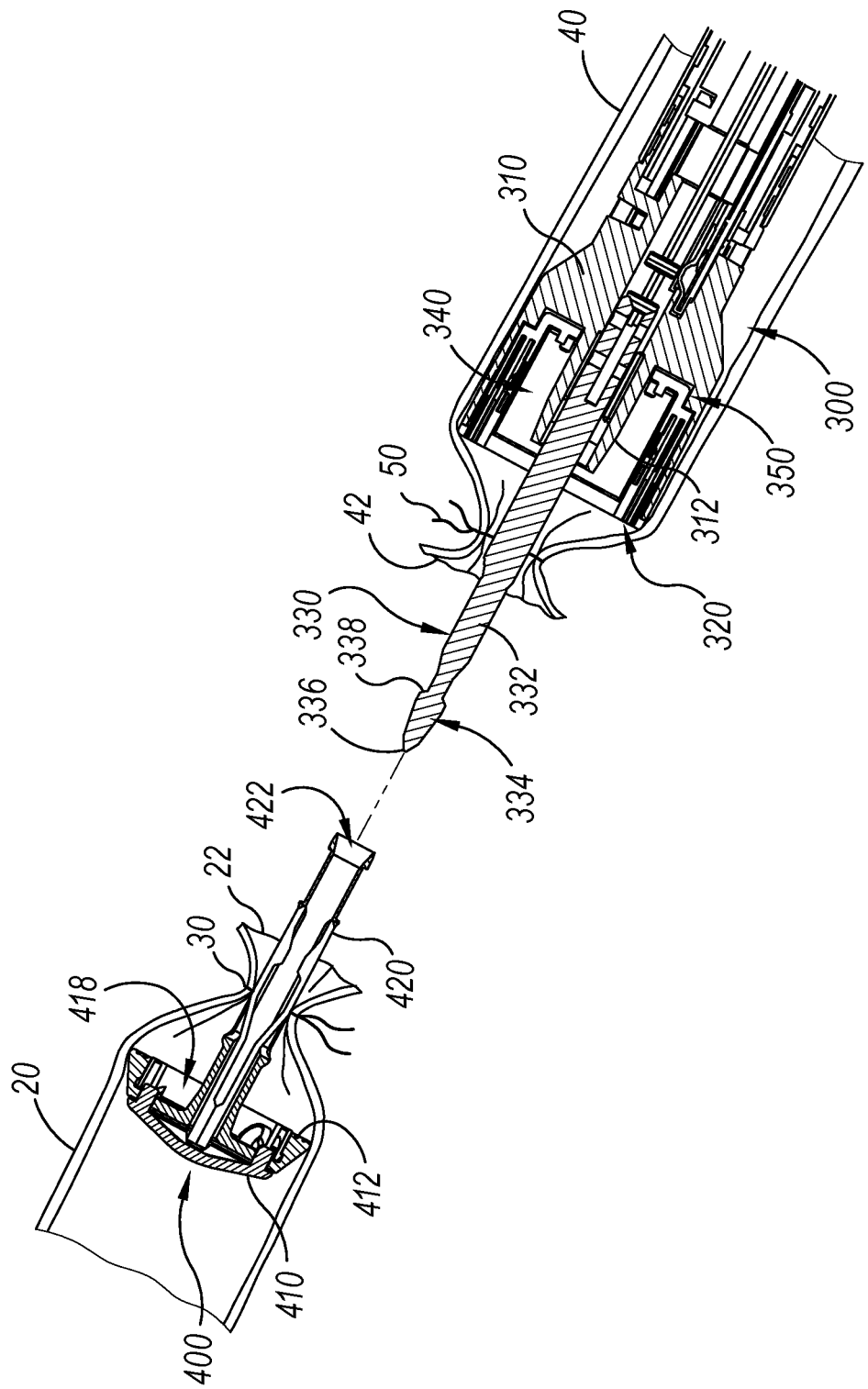
FIG. 7A depicts a cross-sectional side view of the anvil of FIG. 3 positioned within a first section of a digestive tract and the stapling head assembly of FIG. 4 positioned within a separate second section of the digestive tract, with the anvil separated from the stapling head assembly.

As shown in FIG. 7A, anvil (400) is positioned in one tubular anatomical structure (20) and stapling head assembly (300) is positioned in another tubular anatomical structure (40). As shown in FIG. 7A, anvil (400) is positioned in tubular anatomical structure (20) such that shank (420) protrudes from the open severed end (22) of tubular anatomical structure (20). In the present example, purse-string suture (30) is provided about a mid-region of shank (420) to generally secure the position of anvil (400) in tubular anatomical structure (20). Stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40). Stapling head assembly (300) is then urged distally to ensure that stapling head assembly (300) is fully seated at the distal end of tubular anatomical structure (40).

Figure 7B:
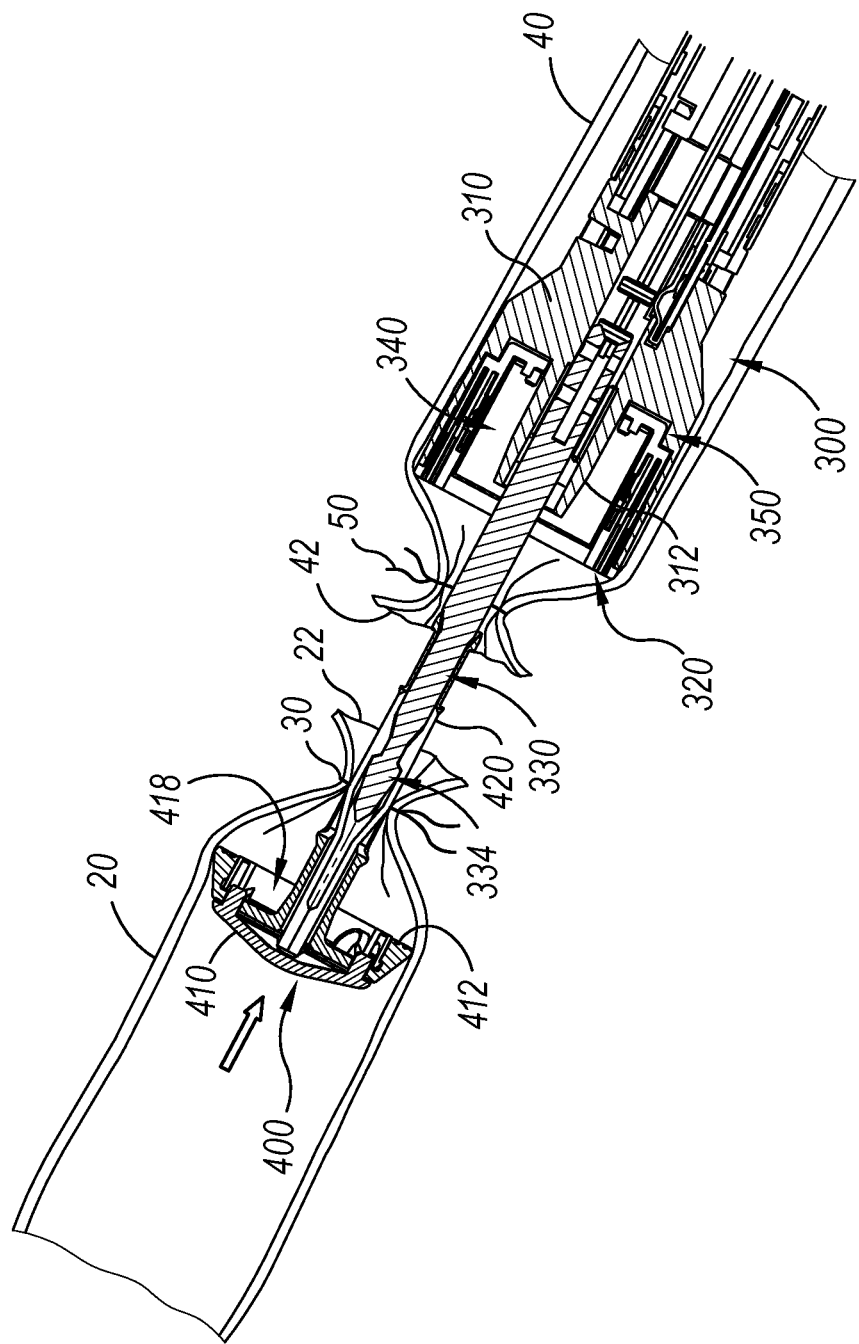
FIG. 7B depicts a cross-sectional side view of the anvil of FIG. 3 positioned within the first section of the digestive tract and the stapling head assembly of FIG. 4 positioned within the separate second section of the digestive tract, with the anvil secured to the stapling head assembly.
Figure 7C:
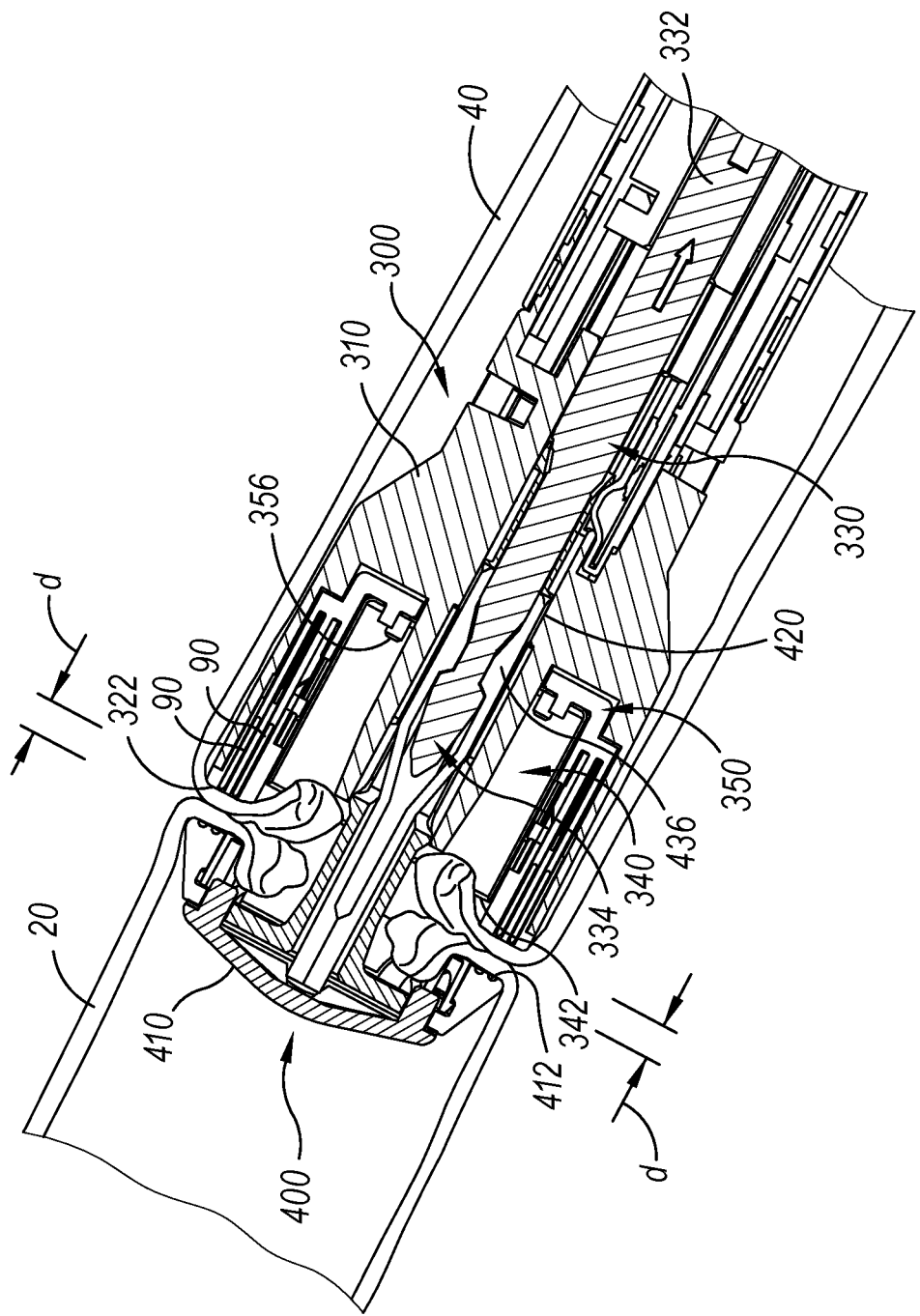
FIG. 7C depicts a cross-sectional side view of the anvil of FIG. 3 positioned within the first section of the digestive tract and the stapling head assembly of FIG. 4 positioned within the separate second section of the digestive tract, with the anvil retracted toward the stapling head assembly to thereby clamp tissue between the anvil and the stapling head assembly.

Next, anvil (400) is secured to trocar (330) by inserting trocar (330) into bore (422) as shown in FIG. 7B. Latch members (430) of anvil (400) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally. As shown in FIG. 7C, this proximal retraction of trocar (330) and anvil (400) compresses the tissue of tubular anatomical structures (20, 40) between surfaces (412, 322) of anvil (400) and stapling head assembly (300). As this occurs, the operator may observe the tactile resistance or feedback via knob (130) while turning knob (130), with such tactile resistance or feedback indicating that the tissue is being compressed. As the tissue is being compressed, the operator may visually observe the position of an indicator needle (not shown) within user interface feature (114) of handle assembly (100) to determine whether the gap distance (d) between opposing surfaces (412, 322) of anvil (400) and stapling head assembly (300) is appropriate; and make any necessary adjustments via knob (130).

Once the operator has appropriately set the gap distance (d) via knob (130), the operator pivots safety trigger (140) toward pistol grip (112) to enable actuation of firing trigger (150). The operator then pivots firing trigger (150) toward pistol grip (112), thus causing firing trigger (150) to actuate the switch of motor activation module (180) and thereby activate motor (160) to rotate. This rotation of motor (160) causes actuation (or "firing") of stapling head assembly (300) by actuating drive bracket (250) distally to thereby drive knife member (340) and staple driver member (350) distally together, as shown in FIG. 7D.

As knife member (340) translates distally, cutting edge (342) of knife member (340) cuts excess tissue that is positioned within annular recess (418) of anvil (400) and the interior of knife member (340). Additionally, washer (417) positioned within annular recess (418) of anvil (400) is broken by knife member (340) when the knife member (340) completes a full distal range of motion from the position shown in FIG. 7C to the position shown in FIG. 7D. It should be understood that washer (417) may also serve as a cutting board for knife member (340) to assist in cutting of tissue.

Figure 7D:
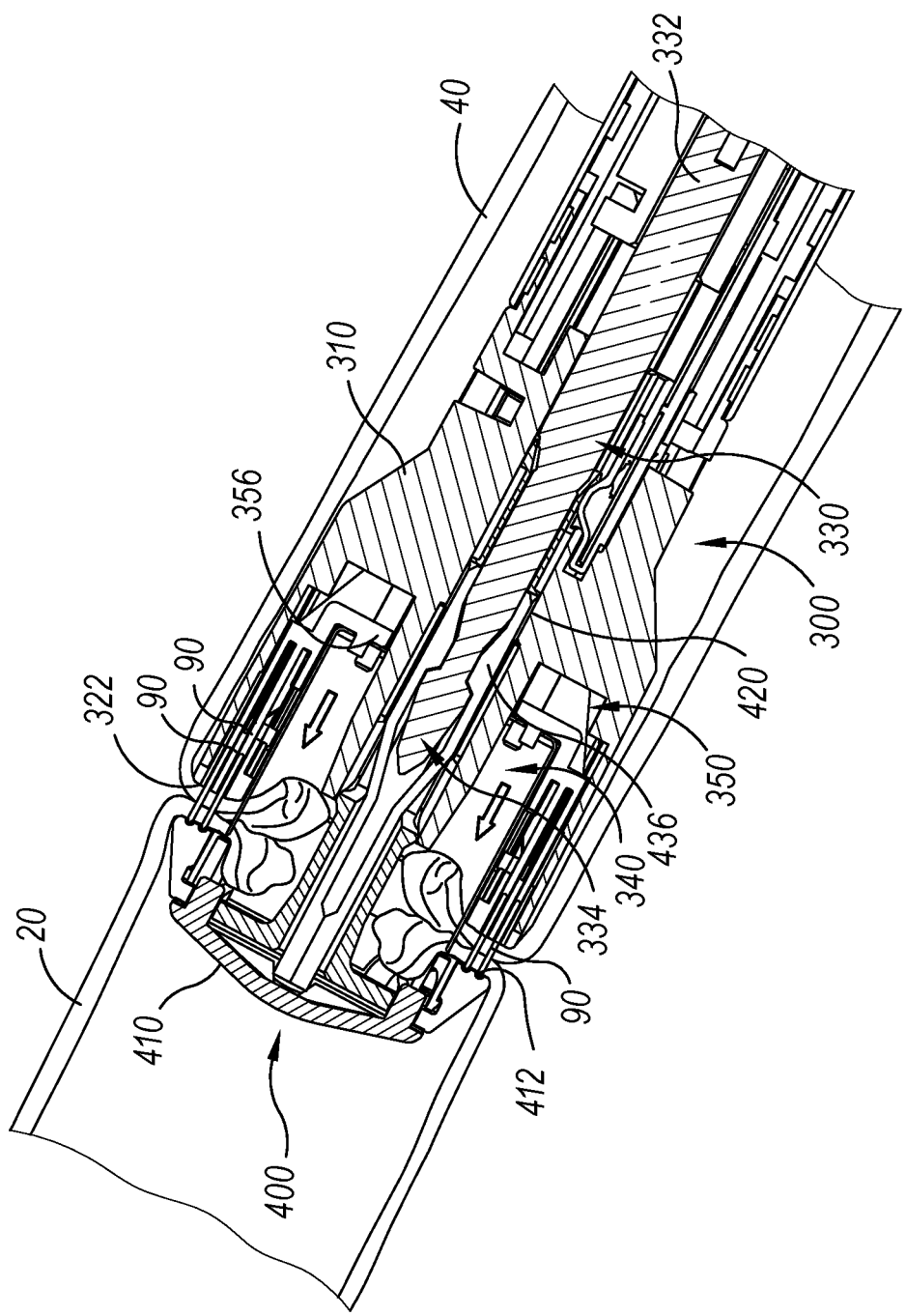
FIG. 7D depicts a cross-sectional side view of the anvil of FIG. 3 positioned within the first section of the digestive tract and the stapling head assembly of FIG. 4 positioned within the second section of the digestive tract, with the stapling head assembly actuated to sever and staple the clamped tissue and thereby joining the first and second sections of the digestive tract.

As staple driver member (350) translates distally from the position shown in FIG. 7C to the position shown in FIG. 7D, staple driver member (350) drives staples (90) through the tissue of tubular anatomical structures (20, 40) and into staple forming pockets (414) of anvil (400). Staple forming pockets (414) deform the driven staples (90) into a "B" shape or a three-dimensional shape, for example, such that the formed staples (90) secure the ends of tissue together, thereby coupling tubular anatomical structure (20) with tubular anatomical structure (40).

Figure 7E:
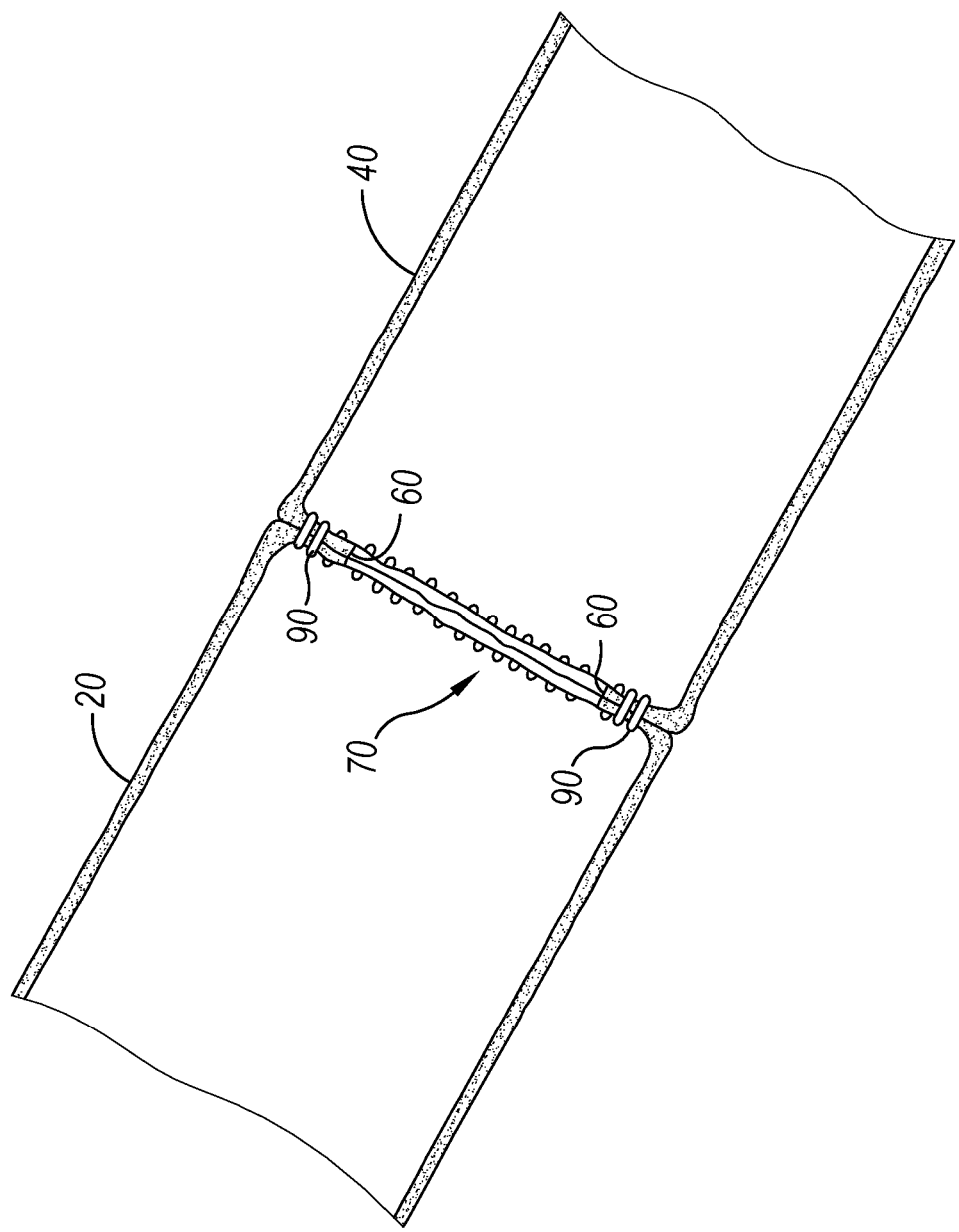
FIG. 7E depicts a cross-sectional side view of the first and second sections of the digestive tract of FIG. 7A joined together at an end-to-end anastomosis formed with the circular stapler of FIG. 1.

After the operator has actuated (or "fired") stapling head assembly (300) as shown in FIG. 7D, the operator rotates knob (130) to drive anvil (400) distally away from stapling head assembly (300), thereby increasing the gap distance (d) to facilitate release of the tissue between surfaces (412, 322). The operator then removes instrument (10) from the patient, with anvil (400) still secured to trocar (330). With instrument (10) removed, the tubular anatomical structures (20, 40) are left secured together by two annular arrays of staples (90) at an anastomosis (70) as shown in FIG. 7E. The inner diameter of the anastomosis (70) is defined by the severed edge (60) left by knife member (340).

II. EXEMPLARY END EFFECTOR HAVING STAPLE FORMING FEATURES ARRANGED IN MULTIPLE ORIENTATIONS

As noted above, the inner diameter of anastomosis (70) formed by instrument (10) is defined by the outer diameter of knife member (340). Because knife member (240) is smaller than the inner diameters of tubular anatomical structures (20, 40), the resulting diameter of anastomosis (70) is generally smaller than that of each tubular anatomical structure (20, 40). Additionally, the configuration of formed staples (90) may inhibit the ability of anastomosis (70) to expand radially.

In some procedures, it may be desirable to form an anastomosis (70) of enlarged diameter and/or to enable the annular arrays of formed staples (90) to expand radially, thereby minimizing strictures, enabling better peristalsis, and minimizing local tension in and resulting damage to the joined portions of tubular anatomical structures (20, 40).

Accordingly, in some such instances, it may be desirable to configure stapling head assembly (300) and anvil (400) with features that enable formation of such an anastomosis and/or patterns of formed staples (90). Exemplary versions of such features are described in greater detail below.

A. Stapling Head Assembly with Alternating Arrays of Staple Forming Features

Figure 8:
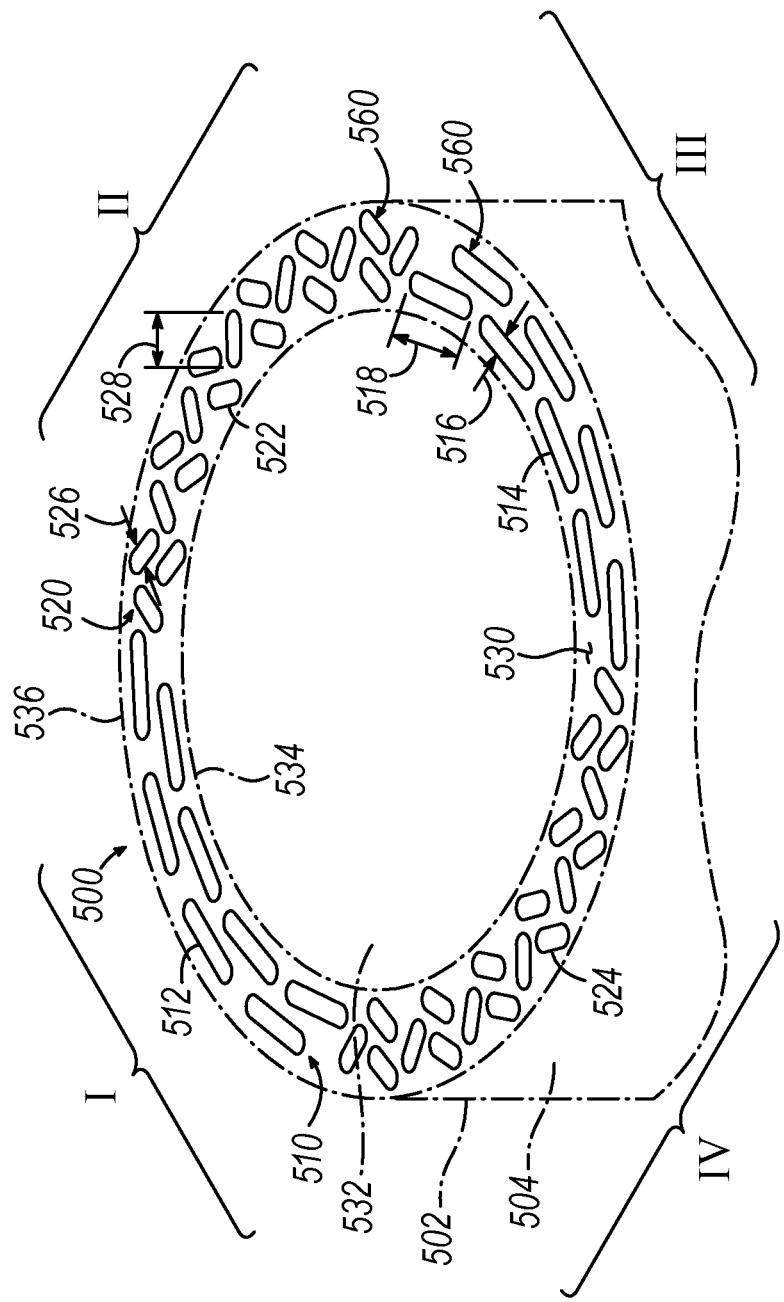
FIG. 8 depicts a schematic perspective view of a distal portion of an exemplary stapling head assembly configured for use with surgical stapler of FIG. 1.

FIG. 8 schematically shows another exemplary stapling head assembly (500) that is configured for use with surgical instrument (10) in place of stapling head assembly (300) described above. Stapling head assembly (500) is similar in structure and function to stapling head assembly (300) except as otherwise described below. In particular, stapling head assembly (500) includes a plurality of arrays (510, 520) of staple openings (560) oriented in different manners such that stapling head assembly (500) is configured to create an anastomosis between tubular anatomical structures (20, 40) of a patient with an annular array of formed staples that is capable of expanding radially outwardly with the stapled tissue. It will be appreciated that stapling head assembly (500) may be used in combination with an anvil (not shown) having similarly arranged arrays of staple forming pockets configured to align with the staple openings of stapling head assembly (500).

Stapling head assembly (500) includes a body member (502) and a deck member (504) disposed at a distal end of body member (502) and having a distally facing surface in the form of a deck surface (530) that surrounds a central longitudinal axis of stapling head assembly (500). Stapling head assembly (500) is shown with portions of the stapling head assembly (500) omitted to show details of the deck surface (530). Deck surface (530) includes an interior perimeter (534), an exterior perimeter (536), and an imaginary centerline (not shown) that is positioned equidistantly between interior perimeter (534) and exterior perimeter (536) and surrounds the central longitudinal axis. Both interior and exterior perimeters (534, 536) are circular in the present example. Interior perimeter (534) defines a lumen (532) that extends proximally through the deck member (504). Though not shown, stapling head assembly (500) may further include a longitudinal actuatable circular knife member and an anvil coupling member in the form of a trocar disposed within lumen (532).

Figure 9:
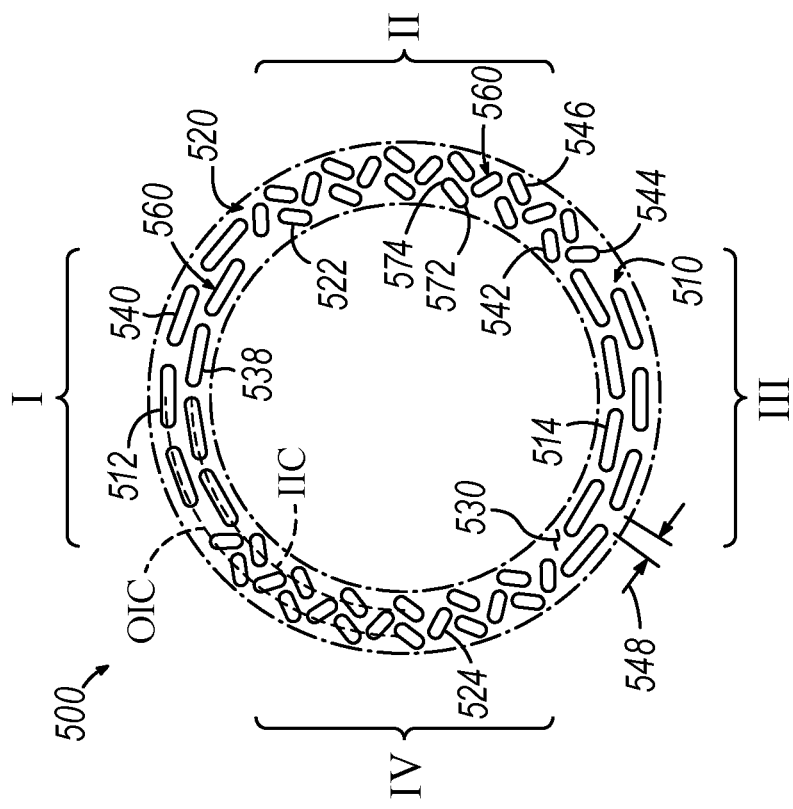
FIG. 9 depicts a top plan view of a deck surface of the stapling head assembly of FIG. 8.

As shown in FIGS. 8 and 9, deck surface (530) further includes a plurality of staple openings (560) that are arranged in a first array (510) and second array (520) about the deck surface (530) in an alternating pattern on circumferentially adjacent deck surface portions, each of which extends along a respective angular range of deck surface (530) about the central longitudinal axis. More specifically, first and second arrays (510, 520) of staple openings (560) are arranged in an alternating manner in quadrants (I, II, III, IV), where each quadrant (I, II, III, IV) extends successively along a respective 90 degree angular range of deck surface (530) about the central longitudinal axis. First and third quadrants (I, III) are diametrically opposed from one another about the central longitudinal axis, and second and fourth quadrants (II, IV) are diametrically opposed from one another about the central longitudinal axis. In the present example, first quadrant (I) includes a first iteration (512) (also referred to herein as a "section") of first array (510) of staple openings (560); second quadrant (II) includes a first iteration (522) of second array (520) of staple openings (560); third quadrant (III) includes a second iteration (514) of first array (510) of staple openings (560); and fourth quadrant (IV) includes a second iteration (524) of second array (520) of staple openings (560). In other words, each quadrant (I, II, III, IV) of deck surface (530) includes a respective array (512, 514, 522, 524) of staple openings (560), where arrays (512, 514) of the first and third quadrants (I, III) have the same first orientation relative to the imaginary centerline of deck surface (530), and where arrays (522, 524) of the second and the fourth quadrants (II, IV) have the same second orientation relative to the imaginary centerline of deck surface (530), where the first and second orientations are different.

FIG. 9 shows deck surface (530) with a first quadrant (I) at the 12 o'clock position, second quadrant (II) in the 3 o'clock position, a third quadrant (III) in the 6 o'clock position, and a fourth quadrant (IV) in the 9 o'clock position. As described above, first array (510) of staple openings (560) includes first and third sections (512, 514), where first section (512) is located in first quadrant (I) of deck surface (530) and third section (514) is located in third quadrant (III) diametrically opposed from first quadrant (I). Second array (520) of staple openings (560) includes second and fourth sections (522, 524), where second section (522) is located in second quadrant (II) of deck surface (530) and fourth section (524) is located in fourth quadrant (IV) of deck surface (530) diametrically opposed from second quadrant (II).

As shown in FIG. 8, in the present version each staple opening (560) of first array (510) has an elongate oval shape having a first width (516) that is generally equal to a second width (526) of staple openings (560) of second array (520). Staple openings (560) of first array (510) have a first length (518) that is longer than, and more specifically approximately twice as long as, a second length (528) of second staple openings (560) of second array (510).

As shown in FIG. 9, each section (512, 514) of first array (510) of staple openings (560) includes a first inner row (538) and a first outer row (540). First inner row (538) lies along an inner imaginary circle (IIC) and first outer row (540) lies along an outer imaginary circle (OIC) arranged concentrically about inner imaginary circle (IIC) and the central longitudinal axis of stapling head assembly (500). Each staple opening (560) of sections (512, 514) of first array (510) is arranged such that a length of the staple opening (560) is tangential to inner or outer imaginary circle (IIC, OIC), respectively, and thus tangential relative to the imaginary centerline of deck surface (530). Additionally, staple openings (560) in first inner row (538) are circumferentially offset from staple openings (560) in first outer row (540) so that staple openings (560) in first inner row (538) align with gaps (548) between adjacent staples openings (560) of the first outer row (540) to ensure effective sealing of the stapled tissue.

Each section (522, 524) of second array (520) of staple openings (560) includes a second inner row (542), a second middle row (544), and a second outer row (546). Second inner row (542) is positioned along inner imaginary circle (IIC). Second outer row (544) is positioned along outer imaginary circle (OIC). Second middle row (546) is positioned between inner imaginary circle (IIC) and outer imaginary circle (OIC), along the imaginary centerline of deck surface (530).

Each staple opening (560) of second inner row (542) is non-tangentially and angularly oriented relative to inner imaginary circle (IIC), and thus to the imaginary deck surface centerline, in a first angular orientation in which a first end (572) is spaced closer to the central longitudinal axis than an opposed second end (574). Similarly, each staple opening (560) of second outer row (546) of second array (520) is non-tangentially and angularly oriented relative to the outer imaginary circle (OIC), and thus to the imaginary deck surface centerline, in the same angular orientation. In the present version, each staple opening (560) in second inner and outer rows (542, 546) is oriented such that its length is angled at approximately 45 degrees relative to the respective inner and outer imaginary circles (IIC, OIC).

In contrast to staple openings (560) of second inner and outer rows (542, 546) of second array (520), each staple opening (560) of second middle row (546) of second array (520) is non-tangentially and angularly oriented relative to inner and outer imaginary circles (IIC, OIC), and thus to the imaginary deck surface centerline, in an opposite angular orientation in which first end (572) of each staple opening (560) is farther from the central longitudinal axis than its second ends (574). In the present version, each of staple opening (560) of the second middle row (574) is angled at approximately 40 degrees relative to the imaginary circles (IIC, OIC) and the deck surface centerline. Accordingly, in the present example, staple openings (560) of second array (520) are arranged in a herringbone pattern and thus are configured to apply a herringbone shaped staple pattern of staples to tissue. The non-tangential, angular orientation of staple openings (560), and thus the corresponding staples (90) deployed into tissue through openings (560), creates an anastomosis (70) in tissue structures (20, 40) about which the formed staples (90) in the stapled regions corresponding to second array (520) are configured to pivot relative to one another about the formed staple legs in the plane of the anastomosis (70). Consequently, the diametrically opposed circumferential portions of the applied staple pattern corresponding to second array (520) are configured to expand radially outwardly with stapled tissue structures (20, 40) during natural radial expansion of tissue structures (20, 40) at anastomosis (70), for example during peristalsis. In some instances, the circumferential portions of tissue structures (20,40) stapled by second array (520) of staple openings (560) may be capable of expanding radially outwardly approximately 125 percent to 200 percent more than the circumferential portions of tissue structures (20, 40) stapled by first array (510) of staple openings (560).

Figure 10:
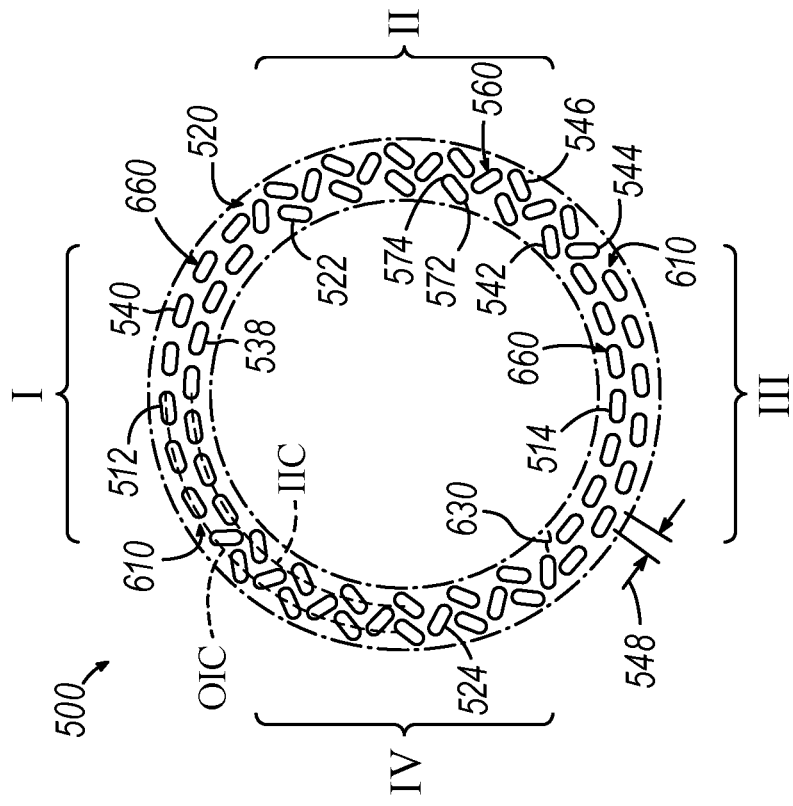
FIG. 10 depicts a top plan view of a second exemplary deck surface configured for use with the stapling head assembly of FIG. 8.

FIG. 10 shows an exemplary alternative deck surface (630) constructed and operable similar to deck surface (530) described above, except as otherwise described below. Deck surface (630) includes a first array (610) of staple openings (660), each of which is shorter in length than staple openings (560) of first array (510) and similar in length to staple openings (560) in second array (520). As a result, the first array (610) of staple openings (660) includes more staple openings (660) than first array (510) such that stapling head assembly (500) need be loaded with only one size of staples.

Figure 11:
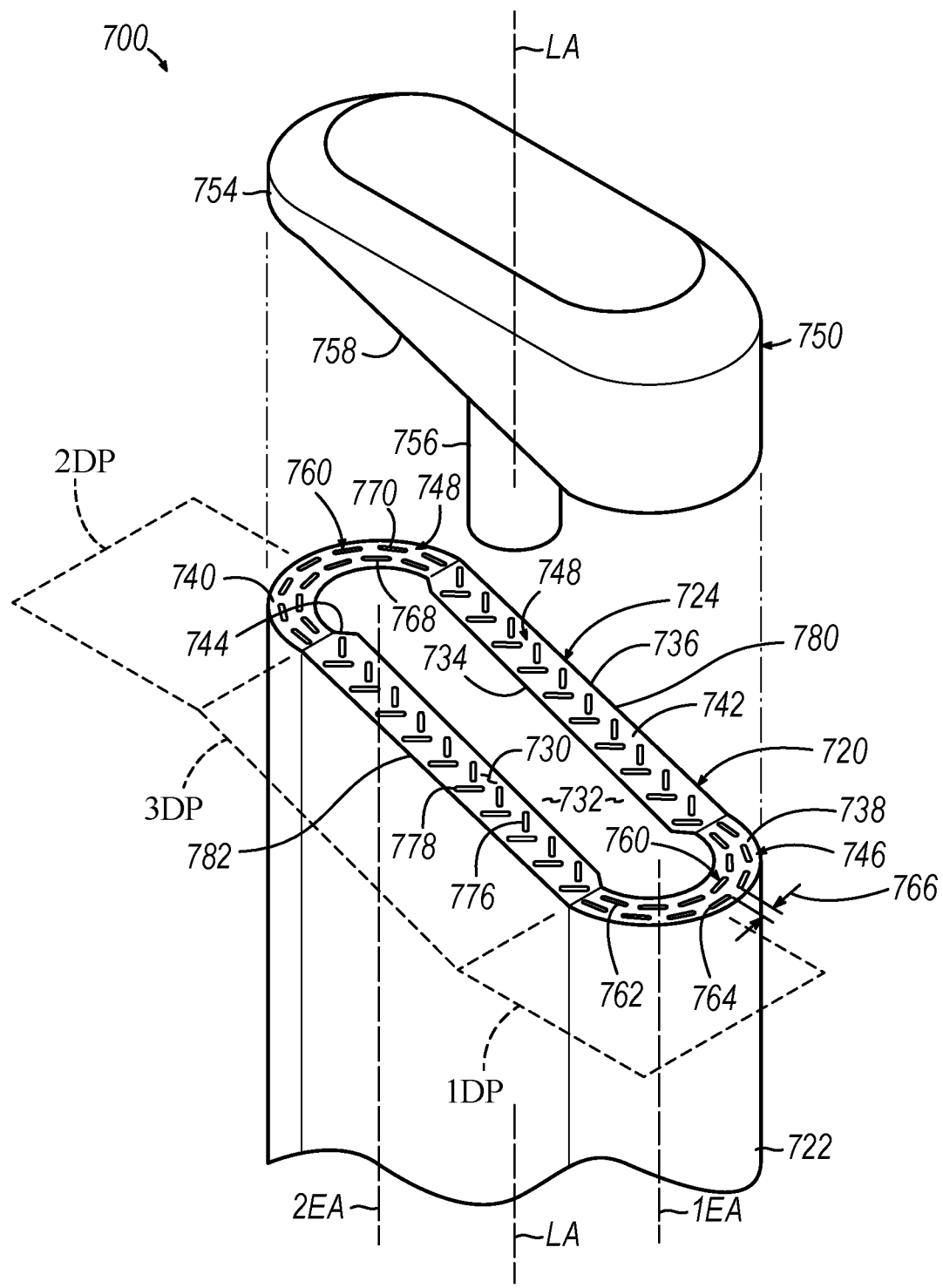
FIG. 11 depicts a schematic perspective view of another exemplary end effector including a stapling head assembly and an anvil configured for use with the surgical stapler of FIG. 1.

B. Second Exemplary End Effector with Alternating Arrays of Staple Forming Features and Stepped Deck Surface In some instances, it may be desirable to substitute a non-circular end effector for use with surgical instrument (10) to facilitate positioning of the end effector within the patient and to form an anastomosis (70) having an enlarged maximum diameter that more effectively facilitates peristalsis within the staple tissue structures (20, 40) at the site of the anastomosis (70). FIG. 11 shows an exemplary end effector (700) having such abilities. End effector (700) includes a stapling head assembly (720) and an anvil (750) configured to releasably couple with stapling head assembly (720) to compress, staple, and cut tissue. Stapling head assembly (720) is similar to stapling head assembly (500) described above except as otherwise described below. Stapling head assembly (720) includes a body member (722) and a deck member (724) having a stepped deck surface (730), and anvil (550) includes a shank (756) and a head (754) having a stepped proximal surface (758) configured to cooperate with stepped deck surface (730) to create an anastomosis (70) of enlarged diameter and having the ability to expand and contract radially with the stapled tissue structures.

FIG. 11 schematically shows non-circular end effector (700) with portions of non-circular stapling head assembly (720) and non-circular anvil (750) omitted to show details of stepped deck member (724) having various arrays of staple openings (760). Non-circular stapling head assembly (720) and non-circular anvil (750) are constructed and operable similar to stapling head assembly (300) and anvil (400) described above, except as otherwise described below.

Non-circular anvil (750) is similar to anvil (400) described above. Non-circular anvil (750) includes a head (754) and shank (756). Shank (756) extends proximally from head (754) and is configured to releasably couple with a coupling feature (not shown), such as an actuatable trocar, of stapling head assembly (720). Head (754) has a non-circular shape that matches the non-circular shape of an exterior profile of the stapling head assembly (720). Proximal surface (758) has a plurality of staple forming pockets (not shown) similar to staple forming pockets (414) described above and configured to align with staple openings (760) of deck member (724). Proximal surface (758) is configured to cooperate with deck surface (730) to clamp and staple tissue.

Figure 12:
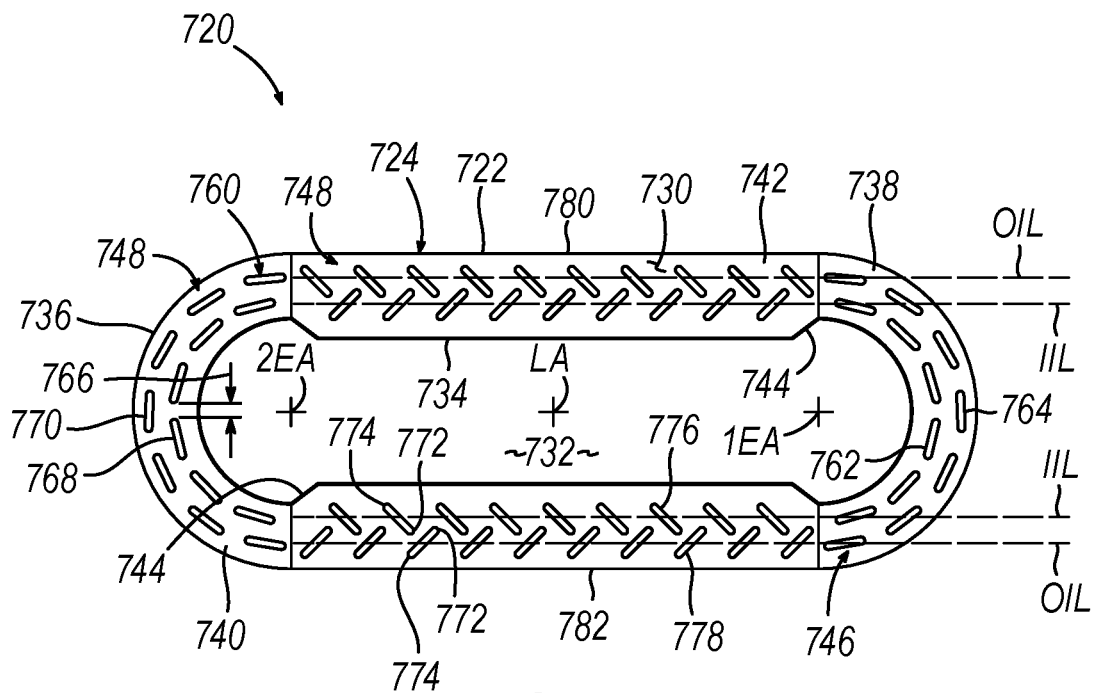
FIG. 12 depicts a top plan view of a deck surface of the stapling head assembly of FIG. 11.
Figure 15:
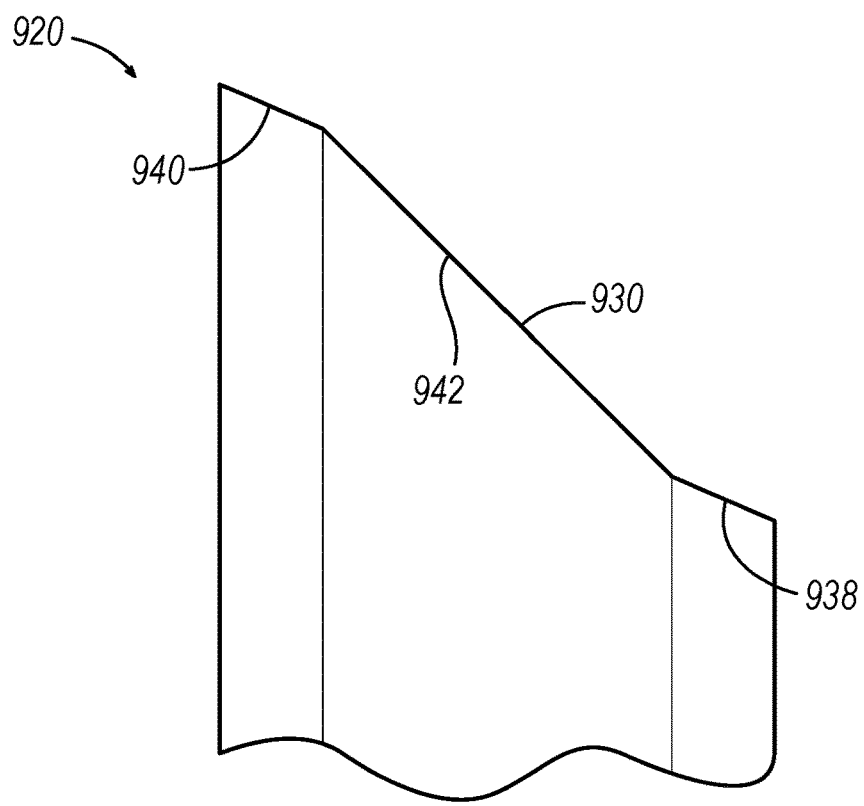
FIG. 15 depicts a side elevational view of another exemplary stapling head assembly including a stepped deck surface.

As shown in FIGS. 11-12, body member (722) extends distally along a central longitudinal axis (LA) of stapling head assembly (720) from distal end of shaft assembly (200). Though not shown, stapling head assembly (720) may further include a knife member and a staple driver member slidably housed within body member (722) similar to knife (340) and staple driver member (350) of stapling head assembly (300). Deck member (724) includes a distally presented stapling surface in the form of a deck surface (730). Deck surface (730) has a non-circular configuration with an exterior perimeter (736) defining a first non-circular shape and an interior perimeter (734) defining a second non-circular shape that is different than the first non-circular shape. In the present example, exterior perimeter (736) has an oval shape, and the interior perimeter has a "dogbone" shape that defines a lumen (732) within body member (722). Deck surface (730) includes a first deck portion (738), a second deck portion (740), and a third deck portion (742), which collectively define an imaginary deck surface centerline (not shown) that surrounds central longitudinal axis (LA) and is spaced equidistantly between interior perimeter (734) and exterior perimeter (736). First deck portion (738) defines and wholly lies in a first deck plane (1DP) that is orthogonal to the central longitudinal axis (LA). Second deck portion (740) defines and wholly lies in a second deck plane (2DP) that is orthogonal to the central longitudinal axis (LA). Second deck plane (2DP) is distally positioned relative to the first deck plane (1DP) and is parallel to the first deck plane (1DP). In other versions, for example as shown in FIG. 15, first deck portion (738) and/or second deck portion (740) may define a corresponding deck plane that is obliquely angled relative to the central longitudinal axis (LA). Third deck portion (742) defines and wholly lies in a third deck plane (3DP) that is obliquely angled relative to the central longitudinal axis (LA) and the first and second deck planes (1DP, 2DP). Third deck portion (742) includes a chamfered interior corner (744) on both ends that transition into the first and second deck portions (738,740), thus providing deck surface (730) with a dog bone shape. In other versions, the interior corner may be rounded.

First deck portion (738) is positioned at a first longitudinal end of third deck portion (742) in a direction transverse to central longitudinal axis (LA). First deck portion (738) has an arcuate, semi-circular shape in first deck plane (1DP) and has a first array (746) of staple openings (760). Each staple opening (760) of first array (746) is tangent to a corresponding semi-circular arcuate portion of the deck surface centerline that extends about a first end axis (1EA), and first array (746) has a first inner row (762) and a first outer row (764). Each staple opening (760) of first outer row (764) is circumferentially indexed around the first end axis (1EA) by a distance that approximately equals half of the length of staple opening (760) in the first inner row (762) so that staple openings (760) of the first inner and outer rows (762,764) overlap in a staple opening gap (766) between adjacent staple openings (760), thus ensure proper sealing of the stapled tissue. It will be appreciated that staple openings (760) on each of deck portions (738, 740, 742) are suitable arranged in such a manner to ensure proper sealing of tissue.

Second deck portion (740) is positioned at an opposite second longitudinal end of the third deck portion (742) in a direction transverse to central longitudinal axis (LA). Similar to first deck portion (738), second deck portion (740) has an arcuate, semi-circular shape in second deck plane (2DP) and has a second array (748) of staple openings (760). Each staple opening (760) of second array (748) is tangent to a corresponding semi-circular arcuate portion of the deck surface centerline that extends about a second end axis (2EA), and second array (748) has a second inner row (768) and a second outer row (770).

Third deck portion (742) is positioned between the first and second deck portions (738, 740) along third deck plane (3DP) and has a linear shape. Third deck portion (742) has a first side (780) located on a first side of the central longitudinal axis (LA) and a second side (782) located on an opposed second side of central longitudinal axis (LA), such that each side (780, 782) is circumferentially adjacent to and interconnects first deck portion (738) and second deck portion (740) on a respective side of central longitudinal axis (LA). Accordingly, it will be appreciated that each of first deck portion (738), second deck portion (740), first side (780) of third deck portion (742), and second side (782) of third deck portion (742) extends along a respective, successive angular range of deck surface (730) about central longitudinal axis (LA). Each side (780, 782) of third deck portion (742) is formed with a greater transverse width, in a plane defined by deck surface (730) and in a direction perpendicular to the imaginary deck surface centerline, than either of first deck portion (738) and second deck portion (740) in order to effectively accommodate staple openings (760) that are orientated angularly relative to the imaginary deck surface centerline, as described in greater detail below.

Each side (780, 782) of third deck portion (742) includes a respective iteration of second array (748) of staple openings (760) having a third inner row (776) and a third outer row (778). Second array of staple openings are collectively arranged in a simplified herringbone pattern in which adjacent staple openings (760) define a V-shape. Third inner row (776) lies along an inner imaginary line (IIL) spaced a first distance from the longitudinal axis (LA) and third outer row (778) lies along an outer imaginary line (OIL) spaced a second distance from the longitudinal axis (LA). Second distance is greater than first distance. Each staple opening (760) of third inner row (776) is oriented in a first angular, non-tangential orientation relative to inner imaginary line (IIC), and each staple opening (760) of third outer row (778) is oriented in an opposite second angular, non-tangential orientation relative to outer imaginary line (OIC). In the present example, staple openings (760) of third inner and outer rows (776, 778) are perpendicular to one another. A first end (772) of each staple opening (760) in third inner row (776) is closer to the longitudinal axis (LA) relative to a second end (774) of each staple opening (760) in third inner row (776). A first end (772) of each staple openings (760) in third outer row (778) is farther from the longitudinal axis (LA) relative to the second end (774) of each staple opening (760) in third outer row (778).

It will be appreciated that any of the exemplary stapling head assemblies described herein, such as stapling head assemblies (720, 820), may be further configured in accordance with any one or more of the teachings of U.S. patent application Ser. No. 17/401,430, entitled "Non-Circular End Effector Features for Circular Surgical Stapler," filed on Aug. 13, 2021, published as U.S. Pub. No. 2023/0045940 on Feb. 16, 2023, the disclosure of which is incorporated by reference herein.

C. Exemplary Stapling Head Assembly with Alternating Arrays of Staple Forming Features and Spacing for Anvil Coupling Feature In some instances, it may be desirable to modify stapling head assembly (720) to incorporate features that provide greater clearance for an actuatable trocar or other anvil coupling feature that is translatable along central longitudinal axis (LA).

Figure 13:
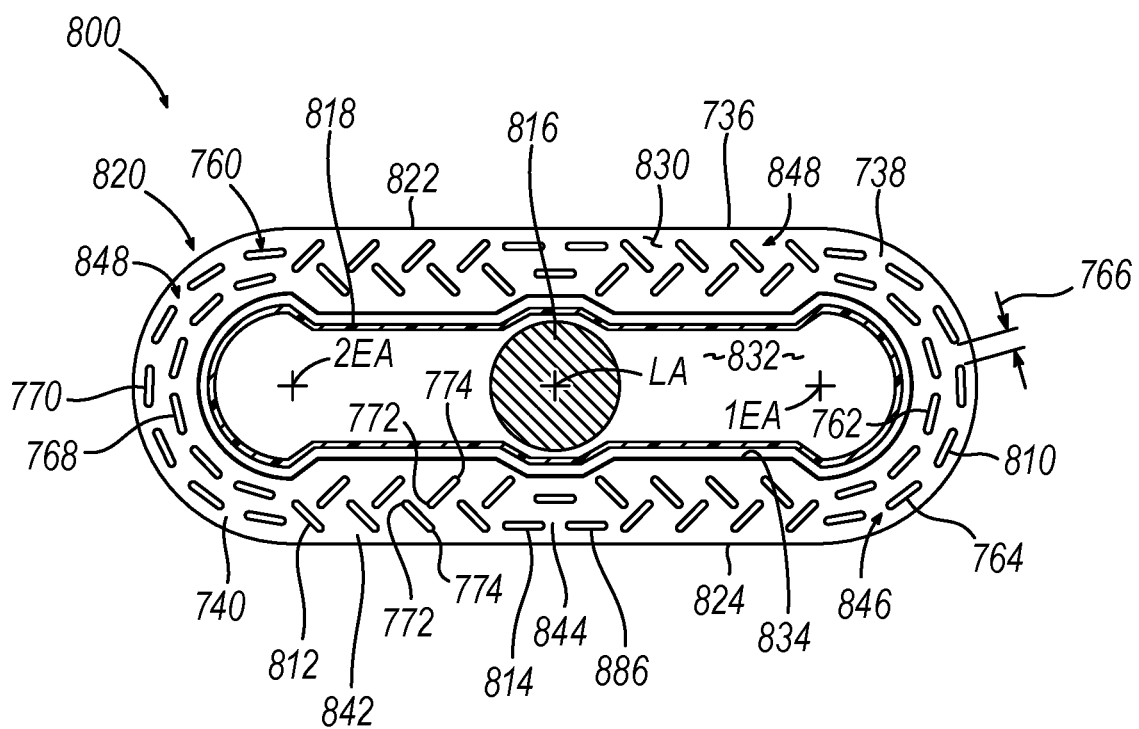
FIG. 13 depicts a top plan view of another exemplary stapling head assembly.

FIG. 13 shows an exemplary alternative stapling head assembly (820) that is constructed and operable similar to stapling head assembly (720) described above, except as otherwise described below. Stapling head assembly (820), like stapling head assembly (720), includes a body member (822) and a deck member (824) having a deck surface (830) with a first deck portion (738), a second portion (740), and a third deck portion (842) that interconnects first deck portion (738) and second deck portion (740). Though not shown, it will be understood that deck member (824) may be angularly stepped similar to deck member (724) described above. Specifically, first deck portion (738) may define a first deck plane that orthogonally intersects central longitudinal axis (LA); second deck portion (740) may define a second deck plane that also orthogonally intersects central longitudinal axis (LA) and thus is parallel with but distal to the first deck plane; and third deck portion (842) may define a third deck plane that is obliquely angled relative to central longitudinal axis (LA) and each of the first and second deck planes. In other versions, deck portions (738, 740, 842) may be coplanar such that deck surface (830) defines a single deck plane that either orthogonally or obliquely intersects central longitudinal axis (LA).

Third deck portion (842) of deck member (824) differs from third deck portion (742) of deck member (724) in that third deck portion (842) includes a pair of central portions (844) diametrically opposed about the central longitudinal axis (LA) and each having a radially outwardly extending recess feature positioned along inner perimeter (834) of deck member (824). As a result, inner perimeter (834) of deck surface (830) steps away from the central longitudinal axis (LA) at each central portion (844) resulting in central portion (844) having a narrower transverse width than other portions of third deck portion (842). In the present version, each central portion (844) deviates from third deck portion (842) with a linear portion of inner perimeter (834) that extends transverse and away from longitudinal axis (LA) and returns to third deck portion (842) with another linear portion that extends at an opposite angle transversely and toward the longitudinal axis (LA). This configuration of central portions (844) provides additional clearance for proximal and distal translation of trocar (816) within lumen (832). In some versions, inner perimeter (834) at central portions (844) may have a round, oval, square, triangular shape, or any additional shape known in the art to provide additional clearance between moving and non-moving members. As shown, knife member (818) is formed with a similar dog bone shape that complements the dog bone shape of interior perimeter (834), for example as disclosed in greater detail in U.S. patent application Ser. No. 17/401,430 filed on Aug. 13, 2021, published as U.S. Pub. No. 2023/0045940 on Feb. 16, 2023, incorporated by reference above.

Each of first deck portion (738) and second deck portion (740) of deck member (824) includes a respective iteration of a first array (810) of staple openings (760) that is similar to first array (746), described above. Each side of third deck portion (842) includes three distinct zones, where staple openings (760) are arranged differently in each zone. A first zone extends between first deck portion (738) and the corresponding central portion (844); a second zone extends between second deck portion (740) and central portion (844); and a third zone extends through central portion (844). Staple openings (760) of the first zone are oriented angularly and non-tangentially relative to the imaginary deck surface centerline in a first simplified herringbone pattern, similar to staple openings (760) in third deck portion (742) of stapling head assembly (720). Staple openings (760) of the second zone are oriented angularly and non-tangentially relative to the imaginary deck surface centerline in a second simplified herringbone pattern (812) that mirrors the first simplified herringbone pattern about an imaginary line that extends through the central longitudinal axis (LA) and bisects each of the central portions (844). Staple openings (760) of the third zone are oriented in a third pattern (814) in which each staple opening (760) extends parallel to the imaginary deck surface centerline.

In each central portion (844) of third deck portion (842), third array (814) of staple openings (760) includes an inner row (884) and an outer row (886). In the present version, Inner row (884) includes a single staple opening (760) that is aligned with central longitudinal axis (LA). In other versions, inner row (884) may include multiple staple openings (760) that span across the linear distance of the central portion (844). Outer row (886) includes two staple openings (760) that define a staple gap (766) between them that is aligned with the single staple opening (760) of inner row (884). It will be appreciated that the staple pattern portions applied to tissue structures (20, 40) by the first and second zones of third deck portion (842) as described above exhibit a greater ability to radially expand and contract than the staple pattern portions applied by the third zone and by first and second deck portions (738, 740).

Figure 14:
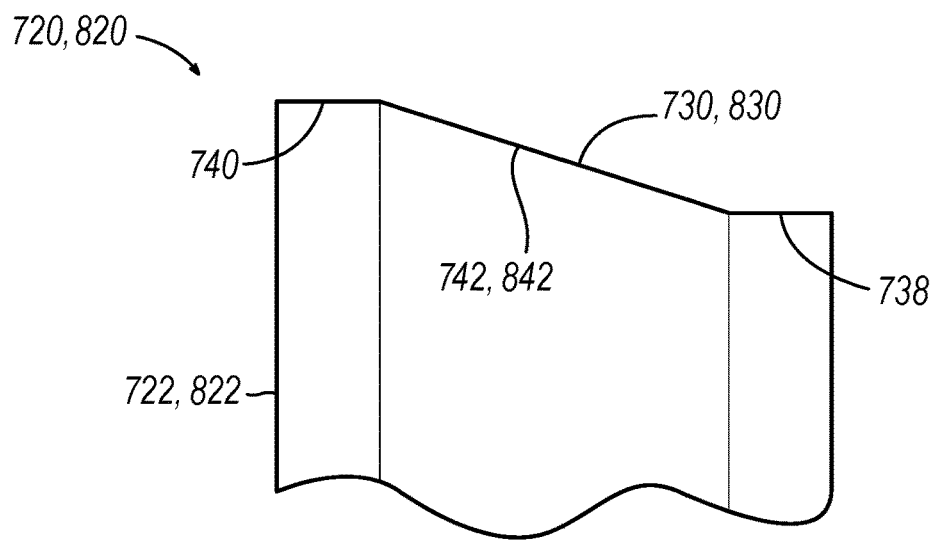
FIG. 14 depicts a side elevational view of the stapling head assemblies of FIGS. 11 and 13, including a stepped deck surface.

FIG. 14 schematically shows stapling head assemblies (720, 820) having a deck surface (730, 830) that is stepped. As described above, deck surface (730, 830) includes first deck portion (738) orthogonal to the central longitudinal axis (LA), second deck portion (740) orthogonal to the central longitudinal axis (LA) and parallel to the first deck portion (738), and third deck portion (742, 842) that is obliquely angled relative to the central longitudinal axis (LA) and each of the first and second deck portions (738, 740).

D. Exemplary Stapling Head Assembly with Obliquely Angled Deck Surface Portions

FIG. 15 schematically shows another exemplary stapling head assembly (920) that is constructed and operable similar to stapling head assemblies (720, 820) described above, except as otherwise described below. Stapling head assembly (920) includes a deck surface (930) having a first deck portion (938) obliquely angled relative to the central longitudinal axis (LA), a second deck portion (940) obliquely angled relative to the longitudinal axis (LA), and a third deck portion (942) obliquely angled relative to the central longitudinal axis (LA). In the present version, third deck portion (942) is more steeply angled relative to central longitudinal axis (LA) than each of first and second deck portions (938, 940), which themselves be oriented at the same oblique angle or different oblique angles relative to central longitudinal axis (LA). It will be appreciated that any suitable angular arrangement of deck portions (938, 940, 942) may be provided in other versions.

E. Exemplary Stapling Head Assembly with Elliptical Deck Member

Figure 16:
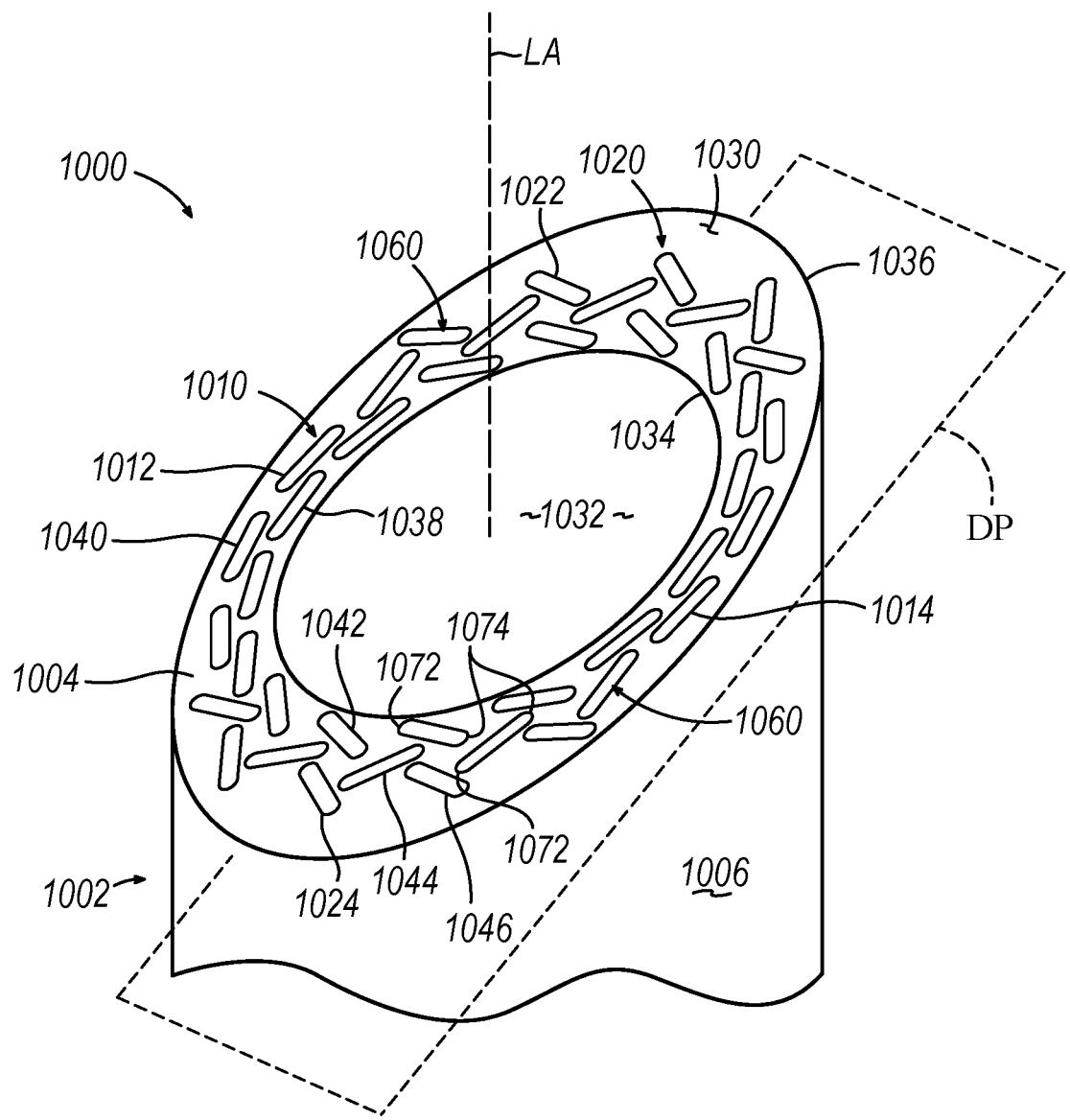
FIG. 16 depicts a schematic perspective view of another exemplary stapling head assembly including an angled elliptical deck surface.
Figure 17:
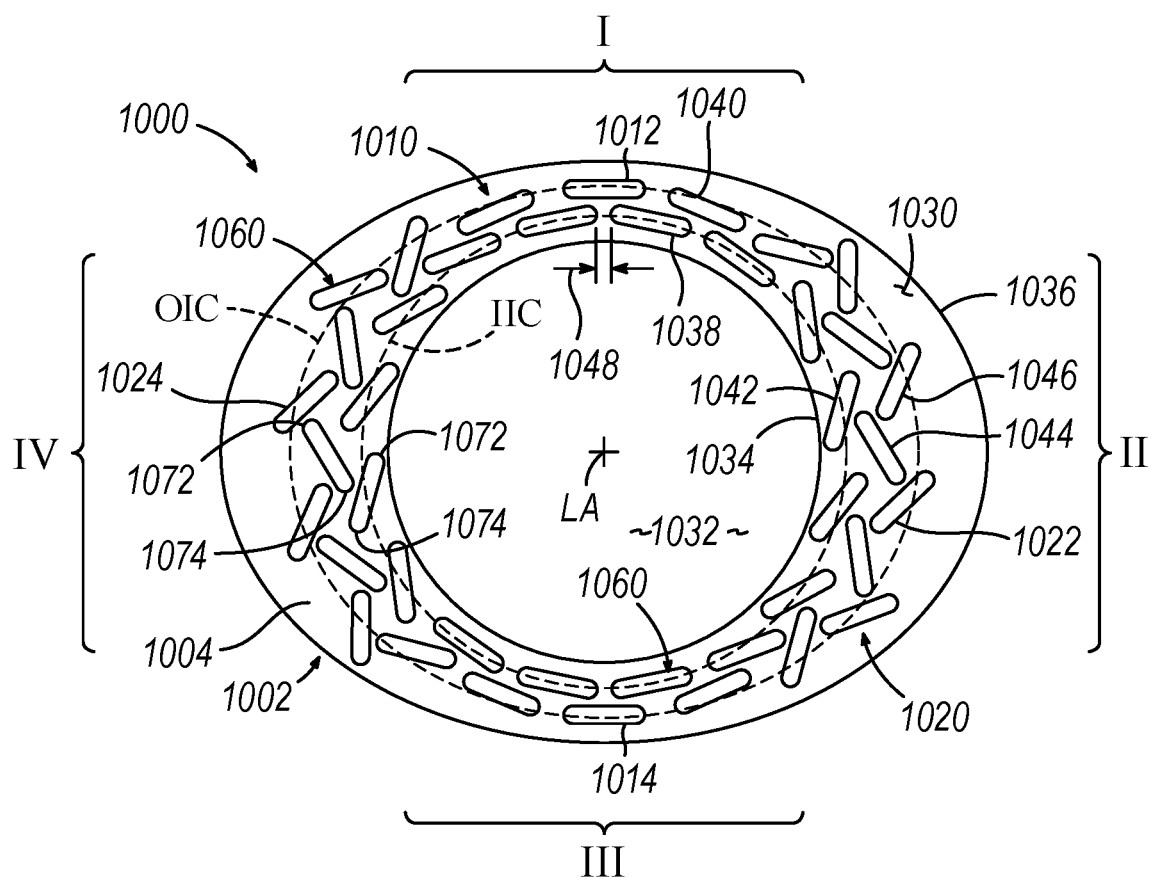
FIG. 17 depicts a top plan view of the elliptical deck surface of the stapling head assembly of FIG. 16.

In some instances, it may be desirable to maintain a circular shaped interior perimeter and a corresponding inner diameter of deck member (320), and a circular shaped exterior perimeter and a corresponding outer diameter of stapling head assembly (300). In some such instances, it may also be desirable to incorporate one or more arrays of staple openings that are obliquely angled relative to an imaginary deck surface centerline of deck member (320) to thereby enable the resulting staple pattern applied to tissue structures (20. 40) to expand and contract radially with the tissue structures (20, 40) at anastomosis (70), for example during peristalsis. FIGS. 16-17 show an exemplary stapling head assembly (1000) having such features and configured for use surgical instrument (10) in place of stapling head assembly (300). It will be appreciated that stapling head assembly (1000) is similar to stapling head assembly (300) except as otherwise described.

Stapling head assembly (1000) includes a body member (1002) operatively attached to the distal end of shaft assembly (200) (see FIG. 1) and having a circular exterior surface (1006). In other versions, body member (1002) may have an oval exterior surface (not shown). Stapling head assembly (1000) further includes an elliptical deck member (1004) having a distally facing surface in the form of an elliptical deck surface (1030).

Elliptical deck surface (1030) defines a deck plane (DP) that is obliquely angled relative to the central longitudinal axis (LA), and includes an interior perimeter (1034) and an exterior perimeter (1036). Interior perimeter (1034) is circular and defines a circular lumen (1032) that extends proximally within the deck member (1004). Exterior perimeter (1036) has an oval shape within deck plane (DP). Elliptical deck surface (1030) includes a first (1010) of staple openings (1060) and a second array (1020) of staple openings (1060) extending through deck surface (1030).

First array (1010) of staple openings (1060) has a first section (1012) and a third section (1014). First section (1012) is located in a first quadrant (I) of the deck surface (1030) and third section (1014) is located in a third quadrant (III) of deck surface (1030) that is diametrically opposed relative to first quadrant (I). Second array (1020) of staple openings (1060) has a second section (1022) and a fourth section (1024). Second section (1022) is located in a second quadrant (II) of the deck surface (1030) and fourth section (1024) is located in a fourth quadrant (IV) of deck surface (1030) that is diametrically opposed relative to second quadrant (II). Second and fourth quadrant (II, IV) are located in a wider portion of deck surface (1030) configured to accommodate the second array (1020) of staple openings (1060) that have a herringbone pattern configured to enable radial expansion and contraction of the corresponding portions of stapled tissue. As described in greater detail below, each staple opening (1060) of first array (1010) located in first and third sections (1012, 1014) extends tangentially to an imaginary deck surface centerline. In contrast, each staple opening (1060) of second array (1020) located in second and fourth sections (1022, 1024) extends obliquely angularly and non-tangentially relative to the imaginary deck surface centerline, defining a herringbone pattern. Accordingly, the staple pattern portions applied to tissue structures (20, 40) by second and fourth sections (1022, 1024) are configured to have a greater degree of radial expandability and contractability than the staple pattern portions applied to tissue structures (20, 40) by first and third sections (1012, 1014).

Staple openings (1060) of first and second arrays (1010, 1020) are sized and configured similarly to staple openings (558) or (560) of stapling head assembly (500) (see FIGS. 8-9). Staple openings (1060) in the first array (1010) may be longer than staple openings (1060) of second array (1020) or may be sized the same as staple openings (660) (see FIG. 10). In the present version, staple openings (1060) of both arrays (1010, 1020) are similarly sized.

First array (1010) of staple openings (1060) includes a first inner row (1038) and a first outer row (1040). Both first and second sections (1012, 1014) have first inner and first outer rows (1038, 1040). First inner row (1038) lies along an inner imaginary circle (IIC). Inner imaginary circle (IIC) is centered around the longitudinal axis (LA). First inner row (1038) is positioned within the first outer row (1040) that lies along an outer imaginary ellipse (OIE). Staple openings (1060) in first inner row (1038) are circumferentially indexed relative to staple openings (1060) in first outer row (1040) and vise-versa so that staple openings (1060) in first outer row (1038) overlap a gap (1048) between staples openings (558) of the first inner row (540).

Second array (1020) of staple openings (1060) includes a second inner row (1042), a second middle row (1044), and a second outer row (1046). Second inner row (1042) is positioned along inner imaginary circle (IIC) and is angularly oriented relative to inner imaginary circle (IIC). Second outer row (1044) is positioned along outer imaginary ellipse (OIE) and is angularly orientated relative to outer imaginary ellipse (OIE). Second middle row (1046) is positioned along inner imaginary ellipse (IIE). Inner imaginary ellipse (IIE) is positioned within outer imaginary ellipse (IIE) and inner imaginary circle (IIC) is concentrically positioned within inner imaginary ellipse (IIE).

Staple openings (560) of second inner row (1042) are non-tangentially angularly oriented relative to inner imaginary circle (IIC) with a first end (1072) that is spaced closer longitudinal axis than the second end (1074). Staple openings (1060) of second outer row (1046) are angularly oriented relative to the outer imaginary ellipse (OIE) oriented at the same angle relative to staple openings (1060) in second inner row (542). In the present version, staple openings (560) in second inner and second outer rows (542, 546) are angled with an offset angle of 45 degrees relative to the respective inner imaginary circle (IIC) and outer imaginary ellipse (IIC, OIE).

Staple openings (1060) of second middle row (1044) are angularly oriented in an opposite direction relative to staple openings (1060) in second inner and outer rows (1042, 1046) resulting in the first ends (1072) of each of staple openings (1060) in second middle row (1044) being farther from longitudinal axis (LA) than second ends (1074). Staple openings (560) of the second middle row (574) are offset at an angle of 40 degrees relative to the inner imaginary ellipse (IIE).

III. EXEMPLARY COMBINATIONS

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a stapling assembly including: (i) a body extending distally along a longitudinal axis, (ii) a deck member disposed at a distal end of the body and defining a deck surface having an imaginary deck surface centerline that surrounds the longitudinal axis, wherein the deck surface includes: (A) a first deck surface portion extending along a first angular range of the deck surface about the longitudinal axis, (B) a second deck surface portion extending along a second angular range of the deck surface about the longitudinal axis, (C) a first array of staple openings disposed on the first deck surface portion and arranged in a first orientation relative to the deck surface centerline, and (D) a second array of staple openings disposed on the second deck surface portion and arranged in a second orientation relative to the deck surface centerline, wherein the second orientation is different than the first orientation, and (iii) a knife member disposed within the body and surrounding the longitudinal axis; and (b) an anvil configured to releasably couple with the stapling assembly to compress tissue against the deck member and form staples in the tissue.

Example 2

The surgical instrument of Example 1, wherein each staple opening of the first array of staple openings is sized differently than each staple opening of the second array of staple openings.

Example 3

The surgical instrument of any of the preceding Examples, wherein the first deck surface portion and the second deck surface portion are circumferentially adjacent.

Example 4

The surgical instrument of any of the preceding Examples, wherein the deck member includes an arcuate portion and a linear portion.

Example 5

The surgical instrument of any of the preceding Examples, wherein each staple opening of the first array of staple openings is oriented tangentially or parallel relative to the deck surface centerline.

Example 6

The surgical instrument of any of the preceding Examples, wherein each staple opening of the second array of staple openings is arranged in a non-tangential angled orientation relative to the deck surface centerline.

Example 7

The surgical instrument of any of the preceding Examples, wherein the second array of staple openings includes a first row of staple openings having a first angular orientation relative to the deck surface centerline and a second row of staple openings having a second angular orientation relative to the deck surface centerline, wherein the first angular orientation is different than the second angular orientation.

Example 8

The surgical instrument of any of the preceding Examples, wherein the second array of staple openings comprises a herringbone pattern.

Example 9

The surgical instrument of any of the preceding Examples, wherein the deck surface defines a deck plane that is obliquely angled relative to the longitudinal axis.

Example 10

The surgical instrument of any of the preceding Examples, wherein the deck surface further includes: (A) a third deck surface portion extending along a third angular range of the deck surface and being opposed from the first deck surface portion about the longitudinal axis, (B) a fourth deck surface portion extending along a fourth angular range of the deck surface and being opposed from the second deck surface portion about the longitudinal axis, (C) a third array of staple openings disposed on the third deck surface portion and arranged in the first orientation relative to the deck surface centerline, and (D) a fourth array of staple openings disposed on the fourth deck surface portion and arranged in the second orientation relative to the deck surface centerline.

Example 11

The surgical instrument of Example 10, wherein the first orientation comprises a tangential or parallel orientation relative to the deck surface centerline, wherein the second orientation comprises an obliquely angled orientation relative to the deck surface centerline.

Example 12

The surgical instrument of any of the preceding Examples, wherein the deck member includes an outer perimeter having an elliptical shape and an inner perimeter having a circular shape.

Example 13

The surgical instrument of any of the preceding Examples, wherein the first deck surface portion defines a first deck plane and the second deck surface portion defines a second deck plane that is angled relative to the first deck plane.

Example 14

The surgical instrument of Example 13, wherein the first deck surface portion has an arcuate shape in the first deck plane and the second deck surface portion has a linear shape in the second deck plane.

Example 15

The surgical instrument of any of Examples 13 through 14, wherein the first deck plane is orthogonal to the longitudinal axis, wherein the second plane is obliquely angled relative to the longitudinal axis.

Example 16

A surgical instrument comprising: (a) a stapling assembly including: (i) a body extending along a longitudinal axis, (ii) a deck member disposed at a distal end of the body and defining a deck surface having an imaginary deck surface centerline that surrounds the longitudinal axis, wherein the deck surface includes: (A) a first array of staple openings disposed on a first deck surface portion, wherein each of the staple openings of the first array is oriented tangentially or parallel relative to the deck surface centerline, and (B) a second array of staple openings disposed on a second deck surface portion circumferentially adjacent to the first deck surface portion, wherein each of the staple openings of the second array is oriented angularly and non-tangentially relative to the deck surface centerline, and (iii) a knife member disposed within the body and surrounding the longitudinal axis; and (c) an anvil configured to releasably couple with the stapling assembly to compress tissue against the deck member and form staples in the tissue.

Example 17

The surgical instrument of Example 16, wherein the first deck surface portion defines a first deck plane and the second deck surface portion defines a second deck plane that is angled relative to the first deck plane.

Example 18

The surgical instrument of any of Examples 16 through 17, wherein the second array of staple openings includes a first row of staple openings and a second row of staple openings arranged outwardly of the first row, wherein each staple opening of the first row is angled in a first angular orientation relative to the deck surface centerline, wherein each staple opening of the second row is angled in a second angular orientation relative to the deck surface centerline, wherein the second angular orientation is different than the first angular orientation.

Example 19

A surgical instrument comprising: (a) a stapling assembly including: (i) a body extending along a longitudinal axis, (ii)

a deck member disposed at a distal end of the body and defining a deck surface having an imaginary deck surface centerline that surrounds the longitudinal axis, wherein the deck surface includes: (A) a first array of staple openings disposed on a first deck surface portion that extends along a first angular range of the deck surface about the longitudinal axis, (B) a second array of staple openings disposed on a second deck surface portion that extends along a second angular range of the deck surface about the longitudinal axis, (C) a third array of staple openings disposed on a third deck surface portion that extends along a third angular range of the deck surface about the longitudinal axis, and (D) a fourth array of staple openings disposed on a fourth deck surface portion that extends along a fourth angular range of the deck surface about the longitudinal axis, wherein the first deck surface portion and the third deck surface portion are opposed about the longitudinal axis, wherein the second deck surface portion and the fourth deck surface portion are opposed about the longitudinal axis, wherein the staple openings of the first array and the third array are arranged in a first orientation relative to the deck surface centerline, wherein the staple openings of the second array and the fourth array are arranged in a second orientation relative to the deck surface centerline, wherein the second orientation is different than the first orientation, and (iii) a knife member disposed within the body and surrounding the longitudinal axis; and (c) an anvil configured to releasably couple with the stapling assembly to compress tissue against the deck member and form staples in the tissue.

Example 20

The surgical instrument of Example 19, wherein each of the staple openings of the first array and the third array is oriented tangentially or parallel relative to the deck surface centerline, wherein each of the staple openings of the second array and the fourth array is oriented angularly and non-tangentially relative to the deck surface centerline.

IV. MISCELLANEOUS

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Additionally, any one or more of the teachings herein may be combined with any one or more of the teachings of U.S. Pat. App. Ser. No. 17/401,391, entitled "Methods of Forming an Anastomosis Between Organs with an Expandable Staple Pattern," filed on Aug. 13, 2021, published as U.S. Pub. No. 2023/0051305 on Feb. 16, 2023; U.S. patent application Ser. No. 17/401,430, entitled "Non-Circular End Effector Features for Circular Surgical Stapler," filed on Aug. 13, 2021, published as U.S. Pub. No. 2023/0045940 on Feb. 16, 2023; U.S. patent application Ser. No. 17/401,439, entitled "Circular Surgical Stapler End Effector Having Staple Line Alignment Feature," filed on Aug. 13, 2021, published as U.S. Pub. No. 2023/0049352 on Feb. 16, 2023; U.S. patent application Ser. No. 17/401,444, entitled "Circular Surgical Stapler for Forming Pattern of Non-Tangential Staples," filed on Aug. 13, 2021, issued as U.S. Pat. No. 11,653,926 on May 23, 2023; U.S. patent application Ser. No. 17/401,451, entitled "Circular Surgical Stapler Having Staples with Expandable Crowns," filed on Aug. 13, 2021, published as U.S. Pub. No. 2023/0051659 on Feb. 16, 2023; and U.S. patent application Ser. No. 17/401,460, entitled "Circular Surgical Stapler for Forming Cross-Pattern of Staples," filed on Aug. 13, 2021, issued as U.S. Pat. No. 11,666,339 on Jun. 6, 2023. The disclosure of each of these US patent documents is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A surgical instrument comprising:
(a) an anvil having a plurality of staple forming pockets configured to form staples; and
(b) a deck configured to cooperate with the anvil to clamp and staple tissue with a plurality of staples, wherein the deck includes:
 (i) a linear deck portion,
 (ii) a first plurality of staple openings disposed in a first zone on the linear deck portion, wherein the staple openings of the first plurality of staple openings are arranged angularly relative to a centerline of the linear deck portion, and
 (iii) a second plurality of staple openings disposed in a second zone adjacent to the first zone on the linear deck portion, wherein the staple openings of the second plurality of staple openings are arranged parallel to the centerline of the linear deck portion,
 wherein a first staple opening of the first plurality of staple openings is positioned a first longitudinal distance from an adjacent second staple opening of the second plurality of staple openings,
 wherein the second staple opening of the second plurality of staple openings is positioned a second longitudinal distance from an adjacent third staple opening of the second plurality of staple openings,
 wherein the first longitudinal distance is different than the second longitudinal distance.

2. The surgical instrument of claim 1, wherein the first longitudinal distance is shorter than the second longitudinal distance.

3. The surgical instrument of claim 1, wherein the first plurality of staple openings is arranged in a herringbone pattern.

4. The surgical instrument of claim 1, wherein the deck and the anvil cooperate to define an end effector having a central axis, wherein the deck extends around the central axis.

5. The surgical instrument of claim 1, wherein the linear deck portion includes a first linear deck portion and a second linear deck portion spaced apart from the first linear deck portion.

6. The surgical instrument of claim 1, wherein the deck includes an arcuate deck portion extending from a portion of the linear deck portion.

7. The surgical instrument of claim 5, wherein the deck defines an opening positioned between the first and second linear deck portions, wherein the surgical instrument further includes a knife member that is actuatable distally through the opening.

8. The surgical instrument of claim 7, wherein the first and second plurality of staple openings are positioned on a first side of the opening.

9. The surgical instrument of claim 5, wherein the deck includes a third plurality of staple openings disposed in a third zone on the second linear deck portion, wherein the staple openings of the third plurality of staple openings are arranged angularly relative to a centerline of the second linear deck portion.

10. The surgical instrument of claim 9, wherein the deck includes a fourth plurality of staple openings disposed in a fourth zone on the second linear deck portion, wherein the staple openings of the fourth plurality of staple openings are arranged parallel to the centerline of the second linear deck portion.

11. The surgical instrument of claim 1, wherein the first zone is arranged on a first side of the second zone, wherein the linear deck portion further includes an additional zone arranged on an opposed second side of the second zone, wherein the first plurality of staple openings is disposed in both the first zone and the additional zone.

12. The surgical instrument of claim 1, wherein the linear deck portion in the first zone includes a first transverse width and the linear deck portion in the second zone includes a second transverse width that differs from the first transverse width.

13. The surgical instrument of claim 12, wherein the first transverse width is larger than the second transverse width.

14. The surgical instrument of claim 5, wherein the deck includes arcuate deck portions, wherein the arcuate deck portions connect the first linear deck portion with the second linear deck portion.

15. The surgical instrument of claim 14, wherein at least one of the arcuate deck portions defines a first deck plane, wherein the first and second linear deck portions define a second deck plane that is angled relative to the first deck plane.

16. A surgical instrument comprising:
(a) an anvil having an anvil surface and a plurality of staple forming pockets configured to form staples; and
(b) a stapling assembly configured to releasably couple with the anvil to compress tissue and form staples in the tissue, wherein the stapling assembly includes:
 (i) a body, and
 (ii) a deck member disposed on a portion of the body and facing the anvil surface, wherein the deck member includes:
  (A) a linear portion,
  (B) a first plurality of staple openings disposed in a first zone on the linear portion, wherein the staple openings of the first plurality of staple openings are arranged in a first array having a first orientation relative to a centerline of the linear portion, and
  (C) a second plurality of staple openings disposed in a second zone on the linear portion, wherein the staple openings of the second plurality of staple openings are arranged in a second array having a second orientation relative to the centerline of the linear portion,
 wherein the first zone is positioned adjacent to the second zone,
 wherein a first staple opening of the first plurality of staple openings and an immediately adjacent second staple opening of the second plurality of staple openings are spaced apart by a first distance,
 wherein the staple openings of the second plurality of staple openings are spaced apart from one another by a second distance that is greater than the first distance.

17. The surgical instrument of claim 16, wherein the first orientation includes an angular orientation of the first plurality of staple openings relative to the centerline of the linear portion.

18. The surgical instrument of claim 16, wherein the second orientation includes a parallel orientation relative to the centerline of the linear portion.

19. A surgical instrument comprising:
   (a) an anvil having a plurality of staple forming pockets configured to form staples; and
   (b) a stapling assembly including:
      (i) a body defining a central axis,
      (ii) a deck member disposed at a distal end of the body and defining a first linear deck surface on a first side of the central axis and a second linear deck surface on a second side of the central axis, wherein the deck member includes:
         (A) a first plurality of staple openings disposed on both the first and second linear deck surfaces, wherein each staple opening of the first plurality of staple openings is angularly oriented relative to a centerline of the respective first or second linear deck surface, and
         (B) a second plurality of staple openings disposed on both the first and second linear deck surfaces, wherein each staple opening of the second plurality of staple openings is parallel to the centerline of the respective first or second linear deck surface; and
      (iii) a knife member disposed within the body and positioned between the first and second linear deck surfaces,
   wherein on each of the first and second linear deck surfaces, a first staple opening of the first plurality of staple openings and an adjacent second staple opening of the second plurality of staple openings are spaced apart by a first distance that is greater than a second distance between each adjacent pair of staple openings of the second plurality of staple openings.

20. The surgical instrument of claim 19, wherein on each of the first and second linear deck surfaces the second plurality of staple openings is longitudinally positioned between first and second groupings of the first plurality of staple openings.

* * * * *